US007645616B2

(12) United States Patent
Xu et al.

(10) Patent No.: US 7,645,616 B2
(45) Date of Patent: Jan. 12, 2010

(54) USE OF LIPOCALIN-2 AS A DIAGNOSTIC MARKER AND THERAPEUTIC TARGET

(75) Inventors: Aimin Xu, Hong Kong (HK); Yu Wang, Hong Kong (HK); Karen Siu Ling Lam, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 11/875,271

(22) Filed: Oct. 19, 2007

(65) Prior Publication Data

US 2008/0095782 A1   Apr. 24, 2008

Related U.S. Application Data

(60) Provisional application No. 60/853,404, filed on Oct. 20, 2006.

(51) Int. Cl.
G01N 33/53 (2006.01)
(52) U.S. Cl. .................. 436/811; 435/7.1; 435/7.92; 436/501
(58) Field of Classification Search ............... 435/6, 435/7.1, 7.92–7.95; 436/501, 518, 811
See application file for complete search history.

(56) References Cited

U.S. PATENT DOCUMENTS

| | | | |
|---|---|---|---|
| 3,832,253 A | 8/1974 | Di Palma et al. | |
| 3,854,480 A | 12/1974 | Zaffaroni | |
| 4,452,775 A | 6/1984 | Kent | |
| 4,667,013 A | 5/1987 | Reichle | |
| 4,675,189 A | 6/1987 | Kent et al. | |
| 4,748,034 A | 5/1988 | de Rham | |
| 5,075,109 A | 12/1991 | Tice et al. | |
| 5,133,974 A | 7/1992 | Paradissis et al. | |
| 5,239,660 A | 8/1993 | Ooi | |
| 5,407,686 A | 4/1995 | Patel et al. | |
| 5,702,902 A | 12/1997 | Tartaglia | |
| 5,736,152 A | 4/1998 | Dunn | |
| 6,919,208 B2 | 7/2005 | Levy et al. | |
| 2003/0157580 A1* | 8/2003 | Hochstrasser et al. | 435/7.93 |
| 2004/0002112 A1 | 1/2004 | Mann et al. | |
| 2004/0132984 A1 | 7/2004 | Dieckman et al. | |
| 2007/0196876 A1* | 8/2007 | Moses et al. | 435/7.23 |

FOREIGN PATENT DOCUMENTS

| | | |
|---|---|---|
| WO | WO 84/03564 | 9/1984 |
| WO | WO 94/05659 | 3/1994 |
| WO | WO 99/20275 | 4/1999 |

OTHER PUBLICATIONS

Forsblad et al., Clinical manifestations of atherosclerosis in an elderly population are related to plasma neopterin, NGAL and endothelin-1, but not to *Chlamydia pneumoniae* serology, International Angiology, Jun. 2002, vol. 21, No. 2, pp. 173-179.*

Elneihoum et al., Leukocyte activation in atherosclerosis: correlation with risk factors, Atherosclerosis, 131, 1997, pp. 79-84.*
Strongin., Laboratory Diagnosis of Viral Infections, Sensitivity, Specificity, and Predictive Value of Diagnostic Tests: Definitions and Clinical Applicatons, Lennette, e., ed., Marcel Dekker, Inc., New Your, pp. 211-219, 1992.*
Akerstrom, et al. "Lipocalins: unity in diversity", *Biochim Biophys Acta.*, 1482(1-2):1-8 (2000).
Bastie, et al. "CD36 in myocytes channels fatty acids to a lipase-accessible triglyceride pool that is related to cell lipid and insulin responsiveness", *Diabetes*, 53:2209-2216 (2004).
Baudry, et al., A., "PKBalpha is required for adipose differentiation of mouse embryonic fibroblasts", *J Cell Sci.*, 119:889-897 (2006).
Berg and Scherer, "Adipose tissue, inflammation, and cardiovascular disease", *Circ Res*, 96:939-949 (2005).
Bratt, et al., "Interactions between neutrophil gelatinase-associated lipocalin and natural lipophilic ligands", *Biochim Biophys Acta.*, 1472(1-2):262-269 (1999).
Cancello, et al., "Reduction of macrophage infiltration and chemoattractant gene expression changes in white adipose tissue of morbidly obese subjects after surgery-induced weight loss", *Diabetes*, 54:2277-2286 (2005).
Devireddy, et al., "Induction of apoptosis by a secreted lipocalin that is transcriptionally regulated by IL-3 deprivation", *Science*, 293:829-834 (2001).
Ellis, et al., "Long-chain acyl-CoA esters as indicators of lipid metabolism and insulin sensitivity in rat and human muscle", *Am J Physiol Endocrinol Metab.*, 279:E554-560 (2000).
Fantuzzi, "Adipose tissue, adipokines, and inflammation", *J Allergy Clin Immunol*, 115:911-919; quiz 920 (2005).
Fisher and Gertow, "Fatty acid transport proteins and insulin resistance", *Curr Opin Lipidol*, 16(2):173-178 (2005).
Flo, et al., Lipocalin 2 mediates an innate immune response to bacterial infection by sequestrating iron *Nature*, 432(7019):917-921 (2004).
Flower, "The lipocalin protein family: structure and function", *Biochem J.*, 318:1-14. (1996).
Fujino, al., "Spermatogonial cell-mediated activation of an IkappaBzeta-independent nuclear factor-kappaB pathway in Sertoli cells induces transcription of the lipocalin-2 gene", *Gene. Mol Endocrinol*, 20:904-915 (2006).
Fukuhara, et al., "Visfatin: a protein secreted by visceral fat that mimics the effects of insulin", *Science*, 307(5708):426-430 (2005).
Hegarty, et al., "The role of intramuscular lipid in insulin resistance" *Acta Physiol Scand*, 178(4):373-383 (2003).
Henikoff and Henikoff, "Amino acid substitution matrices from protein blocks", *Proc. Natl. Acad. Sci. U.S.A.*, 89:10915-10919 (1992).

(Continued)

*Primary Examiner*—Gailene R Gabel
*Assistant Examiner*—Gary W Counts
(74) *Attorney, Agent, or Firm*—Pabst Patent Group LLP

(57) ABSTRACT

Methods and compositions for identifying and treating obesity and obesity-induced metabolic disorders are provided. One aspect provides a method for the evaluation of risk and progression of glucose tolerance, insulin resistance and Type 2 diabetes in mammalian subjects. The method includes measuring the concentration of circulating lipocalin-2 in a subject and comparing the measured level to lipocalin-2 to a reference level. Another aspect provides methods of treating insulin resistance, type 2 diabetes and other related complications by administering to a patient a composition that can reduce the circulating levels of lipocalin-2, for example a lipocalin-2 antagonist.

5 Claims, 8 Drawing Sheets

OTHER PUBLICATIONS

Huang, et al., "Functional silencing of hepatic microsomal glucose-6-phosphatase gene expression in vivo by adenovirus-mediated delivery of short hairpin RNA", *FEBS Lett.*, 558(1-3):69-73 (2004).

Hulver and Dohm, "The molecular mechanism linking muscle fat accumulation to insulin resistance", *Proc Nutr Soc*, 63(2):375-380 (2004).

Jayaraman, et al., "Identification of neutrophil gelatinase-associated lipocalin (NGAL) as a discriminatory marker of the hepatocyte-secreted protein response to IL-1beta: a proteomic analysis", *Biotechnol Bioeng.*, 91:502-515 (2005).

Jessen and Stevens, "Expression profiling during adipocyte differentiation of 3T3-L1 fibroblasts", *Gene*, 299(1-2):95-100 (2002).

Kadowaki and Yamauchi, "Adiponectin and adiponectin receptors", *Endocr Rev*, 26:439-451 (2005).

Kersten, et al., "Peroxisome proliferator-activated receptor alpha mediates the adaptive response to fasting", *J Clin Invest.*, 103(11):1489-1498 (1999).

Kjeldsen, et al. "Isolation and primary structure of NGAL, a novel protein associated with human neutrophil gelatinase", *J Biol Chem.*, 268:10425-10432 (1993).

Kobayashi, "Adipokines: therapeutic targets for metabolic syndrome", *Curr Drug Targets*, 6(4):525-529 (2005).

Kratchmarova, et al., "A proteomic approach for identification of secreted proteins during the differentiation of 3T3-L1 preadipocytes to adipocytes", *Mol Cell Proteomics*, 1:213-222 (2002).

Liu and Nilsen-Hamilton, "Identification of a new acute phase protein" *J Biol Chem.*, 270:22565-22570 (1995).

Lorenz, et al., "Steroid and lipid conjugates of siRNAs to enhance cellular uptake and gene silencing in liver cells", *Bioorg. Med. Chem. Lett.*, 14(19):4975-4977 (2004).

Lowell and Spiegelman, "Towards a molecular understanding of adaptive thermogenesis", *Nature*, 404(6778):652-660 (2000).

Ma, et al., "Nuclease-resistant external guide sequence-induced cleavage of target RNA by human ribonuclease P", *Antisense Nucleic Acid Drug Dev.*, 8(5):415-426 (1998).

Marchesini, et al., "Nonalcoholic fatty liver disease and the metabolic syndrome", *Curr Opin Lipidol.*, 16(4):421-427 (2005).

Matthews, et al., "Homeostasis model assessment: insulin resistance and beta-cell function from fasting plasma glucose and insulin concentrations in man", *Diabetologia*, 28(7):412-419 (1985).

Meheus, et al., "Identification by microsequencing of lipopolysaccharide-induced proteins secreted by mouse macrophages", *J Immunol.*, 151(3):1535-1547 (1993).

Mishra, et al., "Neutrophil gelatinase-associated lipocalin (NGAL) as a biomarker for acute renal injury after cardiac surgery", *Lancet*, 365(9466):1231-1238 (2005).

Needleman and Wunsch, A general method applicable to the search for similarities in the amino acid sequence of two proteins, *J. Mol. Biol.*, 48:443-453 (1970).

Nyce and Metzger, "DNA antisense therapy for asthma in an animal model", *Nature*, 385(6618):721-725 (1997).

Perseghin, "Muscle lipid metabolism in the metabolic syndrome", *Curr Opin Lipidol.*, 16:416(4)-420 (2005).

Rump, et al., "Modification of the plasma clearance and liver uptake of steroid ester-conjugated oligodeoxynucleotides by association with (lactosylated) low-density lipoprotein", *Biochem. Pharmacol.*, 59(11):1407-1416 (2000).

Soutschek, et al., "Therapeutic silencing of an endogenous gene by systemic administration of modified siRNAs", *Nature*, 432(7014):173-178 (2004).

Tan, et al., "C-reactive protein predicts the deterioration of glycemia in chinese subjects with impaired glucose tolerance", *Diabetes Care*, 26:2323-2328 (2003).

Tataranni and Ortega, "A burning question: does an adipokine-induced activation of the immune system mediate the effect of overnutrition on type 2 diabetes?", *Diabetes*, 54(4):917-927 (2005).

Tomas, et al., "Enhanced muscle fat oxidation and glucose transport by ACRP30 globular domain: acetyl-CoA carboxylase inhibition and AMP-activated protein kinase activation.", *Proc Natl Acad Sci U S A*, 99:16309-16313 (2002).

Trayhurn and Wood, "Adipokines: inflammation and the pleiotropic role of white adipose tissue", *Br J Nutr*, 92(3):347-355 (2004).

Wang, et al., "Hydroxylation and glycosylation of the four conserved lysine residues in the collagenous domain of adiponectin. Potential role in the modulation of its insulin-sensitizing activity", *J. Biol Chem*, 277:19521-29 (2002).

Weisberg, et al., "Obesity is associated with macrophage accumulation in adipose tissue", *J Clin Invest*, 112:1796-1808 (2003).

Wellen and Hotamisligil, "Inflammation, stress, and diabetes", *J Clin Invest*, 115(5):1111-1119 (2005).

Xu, et al., "Angiopoietin-like protein 4 decreases blood glucose and improves glucose tolerance but induces hyperlipidemia and hepatic steatosis in mice", *Proc Natl Acad Sci U S A*, 102:6086-6091 (2005).

Xu, et al., "The fat-derived hormone adiponectin alleviates alcoholic and nonalcoholic fatty liver diseases in mice", *J Clin Invest*, 112:91-100 (2003).

Xu, et al., "Chronic inflammation in fat plays a crucial role in the development of obesity-related insulin resistance", *J Clin Invest*, 112:1821-1830 (2003).

Yamauchi, et al., "The fat-derived hormone adiponectin reverses insulin resistance associated with both lipoatrophy and obesity", *Nat Med*, 7:941-946 (2001).

Yang, et al, "Serum retinol binding protein 4 contributes to insulin resistance in obesity and type 2 diabetes", *Nature*, 436:356-362 (2005).

Yan, et al., "The high weight urinary matrix metalloproteinase (MMP) activity is a complex of gelatinase B/MMP-9 and neutrophil gelatinase-associated lipocalin (NGAL)", *J. Biol. Chem.*, 276(40):37258-37265 (2001).

Alain A. Mir, et al., "A search for candidate genes for lipodystrophy, obesity and diabetes via gene expression analysis of A-ZIP/F-1 mice", *Genomics*, 84(4):378-390 (2003).

Bart A. Jessen, et al., "Expression profiling during adipocyte differentiation of 3T3-L1 fibroblasts", *Gene*, 299:95-100 (2002).

Ying Lin, et al., Hyperglycemia-induced production of acute phase reactants in adipose tissue, Journal of Biological Chemistry, 276(45):42077-42083 (2001).

* cited by examiner

Muscle

SEQUENCE LISTING

<160> NUMBER OF SEQ ID NOS: 6

<210> SEQ ID NO 1
<211> LENGTH: 198
<212> TYPE: PRT
<213> ORGANISM: Homo sapiens

<400> SEQUENCE: 1

```
Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
                100                 105                 110

Thr Leu Gly Asn Ile Lys Ser Tyr Pro Gly Leu Thr Ser Tyr Leu Val
            115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
            195

<210> SEQ ID NO 2
<211> LENGTH: 840
<212> TYPE: DNA
<213> ORGANISM: Homo sapiens

<400> SEQUENCE: 2
actcgccacc tcctcttcca ccctgccag gcccagcagc caccacagcg cctgcttcct      60
cggccctgaa atcatgcccc taggtctcct gtggctgggc ctagccctgt tggggctct    120
gcatgcccag gcccaggact ccacctcaga cctgatccca gccccacctc tgagcaaggt   180
ccctctgcag cagaacttcc aggacaacca attccagggg aagtggtatg tggtaggcct   240
ggcagggaat gcaattctca gagaagacaa agacccgcaa aagatgtatg ccaccatcta   300
tgagctgaaa gaagacaaga gctacaatgt cacctccgtc ctgtttagga aaaagaagtg   360
tgactactgg atcaggactt ttgttccagg ttgccagccc ggcgagttca cgctgggcaa   420
cattaagagt taccctggat taacgagtta cctcgtccga gtggtgagca ccaactacaa   480
ccagcatgct atggtgttct tcaagaaagt ttctcaaaac agggagtact caagatcac    540
cctctacggg agaaccaagg agctgacttc ggaactaaag gagaacttca tccgcttctc   600
caaatctctg ggcctcc ctg aaaaccacat cgtcttccct gtcccaatcg accagtgtat   660
cgacggctga gtgcacaggt gccgccagct gccgcaccag cccgaacacc attgagggag   720
ctggagacc ctccccacag tgccacccat gcagctgctc cccaggccac cccgctgatg    780
gagccccacc ttgtctgcta ataaacatg tgccctcagg ccaaaaaaaa aaaaaaaaaa    840

<210> SEQ ID NO 3
<211> LENGTH: 31
<212> TYPE: DNA
```

```
<213> ORGANISM: artificial sequence
<220> FEATURE:
<223> OTHER INFORMATION: synthetic primer

<400> SEQUENCE: 3
agtaggatcc caggactcaa ctcagaactt g                              31

<210> SEQ ID NO 4
<211> LENGTH: 31
<212> TYPE: DNA
<213> ORGANISM: artificial sequence
<220> FEATURE:
<223> OTHER INFORMATION: synthetic primer

<400> SEQUENCE: 4
agtactcgag tcagttgtca atgcattggt c                              31

<210> SEQ ID NO 5
<211> LENGTH: 29
<212> TYPE: DNA
<213> ORGANISM: artificial sequence
<220> FEATURE:
<223> OTHER INFORMATION: synthetic primer

<400> SEQUENCE: 5
tgcaggatcc caggactcca cctcagacc                                 29

<210> SEQ ID NO 6
<211> LENGTH: 32
<212> TYPE: DNA
<213> ORGANISM: artificial sequence
<220> FEATURE:
<223> OTHER INFORMATION: synthetic primer

<400> SEQUENCE: 6
tagcctcgag tcagccgtcg atacactggt cg                             32
```

USE OF LIPOCALIN-2 AS A DIAGNOSTIC MARKER AND THERAPEUTIC TARGET

CROSS REFERENCE TO RELATED APPLICATION

This application claims benefit of and priority to U.S. Provisional Patent Application No. 60/853,404 filed Oct. 20, 2006, and where permissible is incorporated by reference herein in its entirety.

FIELD OF THE INVENTION

Aspects of the present invention are generally directed to the use of lipocalin-2 or a variant thereof as a diagnostic marker and therapeutic target, for example in obesity and obesity-induced metabolic disorders such as insulin resistance and type 2 diabetes.

BACKGROUND OF THE INVENTION

According to the World Health Organization obesity has reached epidemic proportions globally, with more than 1 billion adults overweight. At least 300 million of them are clinically obese, and obesity is a major contributor to the global burden of chronic disease and disability. For example, obesity is the most common risk factor for insulin resistance, type 2 Diabetes Mellitus (T2DM) and cardiovascular disorders. Results from the 1999-2002 National Health and Nutrition Examination Survey (NHANES), using measured heights and weights, indicate that an estimated 65 percent of U.S. adults are either overweight or obese. Because millions of adults suffer from obesity or obesity-induced metabolic disorders, new methods for predicting adults at risk for obesity and new compositions for treating obesity and obesity-induced metabolic disorders are in high demand.

Although the detailed molecular events that link obesity with its associated pathologies are not well understood, accumulating evidence suggest that systemic inflammation might be an important mediator (Berg, A. H., and Scherer, P. E., *Circ Res*, 96:939-949 (2005); Wellen, K. E., and Hotamisligil, G. S., *J Clin Invest*, 115:1111-1119 (2005)). Studies on both human subjects and animal models have demonstrated a close association between obesity and a state of low-grade, chronic inflammation, which is characterized by macrophage infiltration in adipose tissue and elevated circulating concentrations of pro-inflammatory molecules, including acute phase proteins, cytokines, adiopkines and chemokines (Tataranni, P. A., and Ortega, E., *Diabetes*, 54:917-927 2005); Cancello, R., et al., *Diabetes*, 54:2277-2286 (2005); Xu, H., et al., *J Clin Invest*, 112:1821-1830 (2003); Weisberg, S. P., et al. *J Clin Invest*, 112:1796-1808 (2003)).

In obese states, pro-inflammatory factors are produced predominantly from enlarged adipocytes and activated macrophages in adipose tissue and liver. Many of these inflammatory factors, such as interleukin (IL) 6, TNFα, resistin and retinol-binding protein 4 (RBP4), can directly induce glucose intolerance and insulin resistance by antagonizing metabolic actions of insulin at peripheral tissues, especially in liver and skeletal muscle (Trayhurn, P., and Wood, I. S. *Br J Nutr*, 92:347-355 (2004); Fantuzzi, G. *J Allergy Clin Immunol*, 115:911-919; quiz 920 (2005); Yang, Q., et al, *Nature*, 436:356-362 (2005)). On the other hand, several other adipokines produced from adipocytes, including adiponectin and visfatin, possess insulin-sensitizing activity and exert beneficial effects on glucose and lipid homeostasis (Kobayashi, K., *Curr Drug Targets*, 6:525-529 (2005); Kadowaki, T., and Yamauchi, T., *Endocr Rev*, 26:439-451 (2005); Fukuhara, A., et al., *Science*, 307:426-430 (2005).

Therefore, it is an object of the invention to provide compositions and methods for assessing the propensity to develop obesity or obesity-induced metabolic disorders.

It is another object to provide compositions and methods for assisting in the diagnosis of obesity or obesity-induced metabolic disorders.

It is still another object to provide methods and compositions for the treatment of obesity or obesity-induced metabolic disorders.

It is another object to provide methods for identifying modulators of lipocalin-2 or a variant thereof.

SUMMARY OF THE INVENTION

Methods and compositions for identifying and treating obesity and obesity-induced metabolic disorders are provided. One aspect provides a method for the evaluation of risk and progression of glucose tolerance, insulin resistance and Type 2 diabetes in mammalian subjects. The method includes measuring the concentration of circulating lipocalin-2 in a subject and comparing the measured level to a lipocalin-2 reference level. Levels of lipocalin-2 that are higher than the reference level are indicative of an increased risk or propensity of developing obesity or an obesity-induced metabolic disorder. Another aspect provides methods of treating obesity or an obesity-induced metabolic disorder such as insulin resistance, type 2 diabetes and other related complications by administering to a patient a composition that can reduce the circulating levels of lipocalin-2, for example, a lipocalin-2 antagonist.

Still another aspect provides a method for diagnosing or aiding in the diagnosis of obesity and/or an obesity-induced metabolic disorder in a subject. The method includes obtaining a blood sample from the subject and determining the lipocalin-2 level contained in the blood sample. The determined levels are compared to a reference level. In a preferred aspect, obesity, hyperglycemia or insulin resistance is present if the lipocalin-2 level is higher than the reference level. In another preferred embodiment, the lipocalin-2 level in the blood sample is measured by a sandwich immunoassay.

Still another aspect provides a method of screening substances useful for treating diseases such as hyperglycemia, glucose intolerance and insulin resistance. The method includes contacting a mammalian cell expressing a lipocalin-2 polypeptide with test substances, determining whether lipocalin-2 polypeptide expression is decreased by the test substances, and selecting the substances that decrease lipocalin-2 expression.

Another aspect provides a method of treating, inhibiting or preventing obesity and or obesity induced metabolic disorder by administering to a subject an agent capable of reducing lipocalin-2 activity.

BRIEF DESCRIPTION OF THE DRAWINGS

FIG. 3A shows the result of glucose tolerance test at day 24 after treatments. FIG. 3B shows the result of insulin tolerance test at day 26 after treatment. P<0.05 versus vehicle-treated mice.

* P<0.05; ** P<0.01 versus untreated cells.

Figure 6:
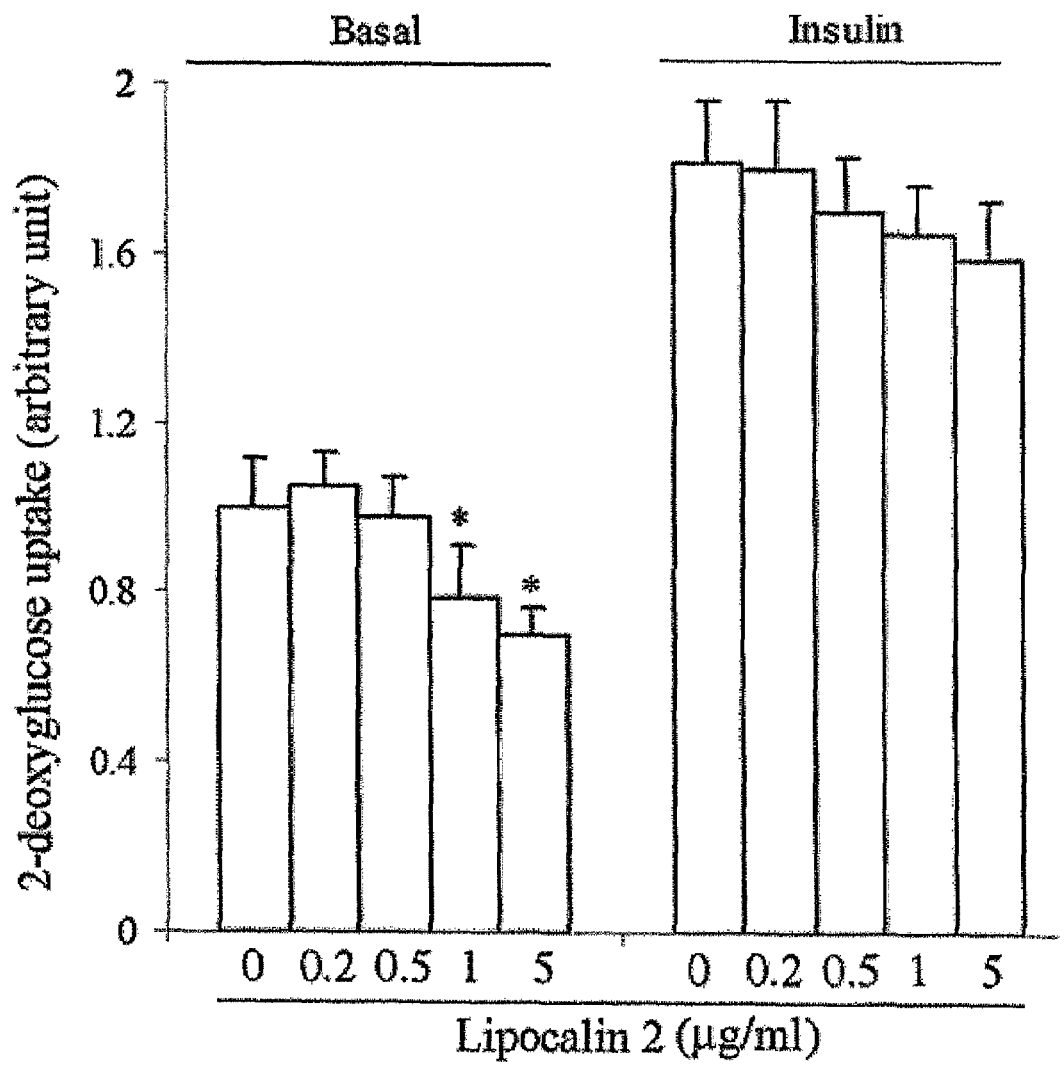

FIG. 6 is a bar graph of 2-deoxyglucose uptake (arbitrary units) in L6 myotubes treated without or with indicated concentrations of lipocalin-2 for 48 hr, and then stimulated without or with insulin for another 20 min. The rate of glucose uptake was measured by uptake of 2-deoxy-D-[$^3$H]glucose. * P<0.05 versus untreated cells; # P<0.05 versus cells treated with insulin alone (n=4-6).

Figure 7A:
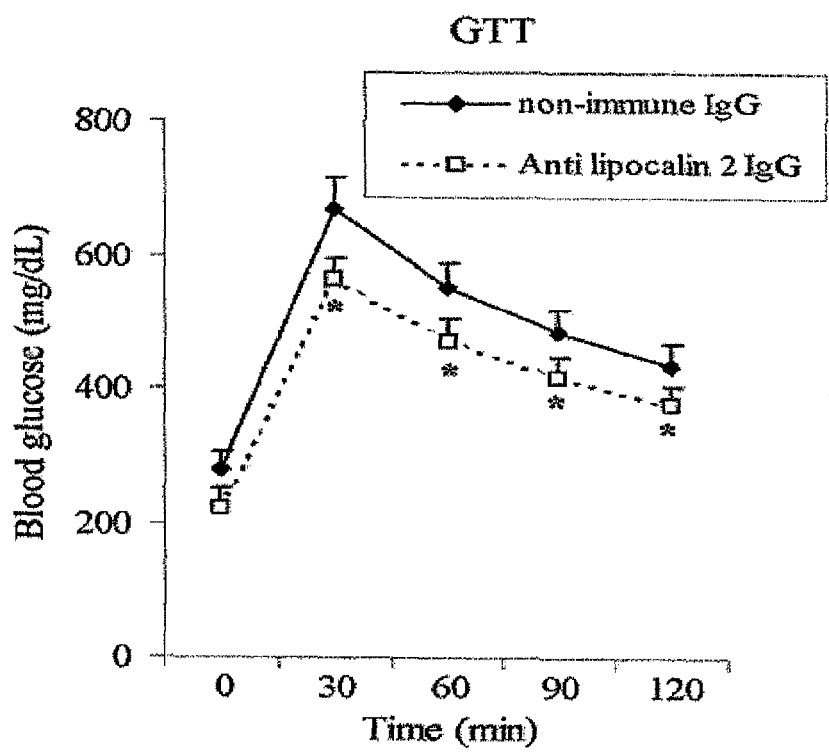
Figure 7B:
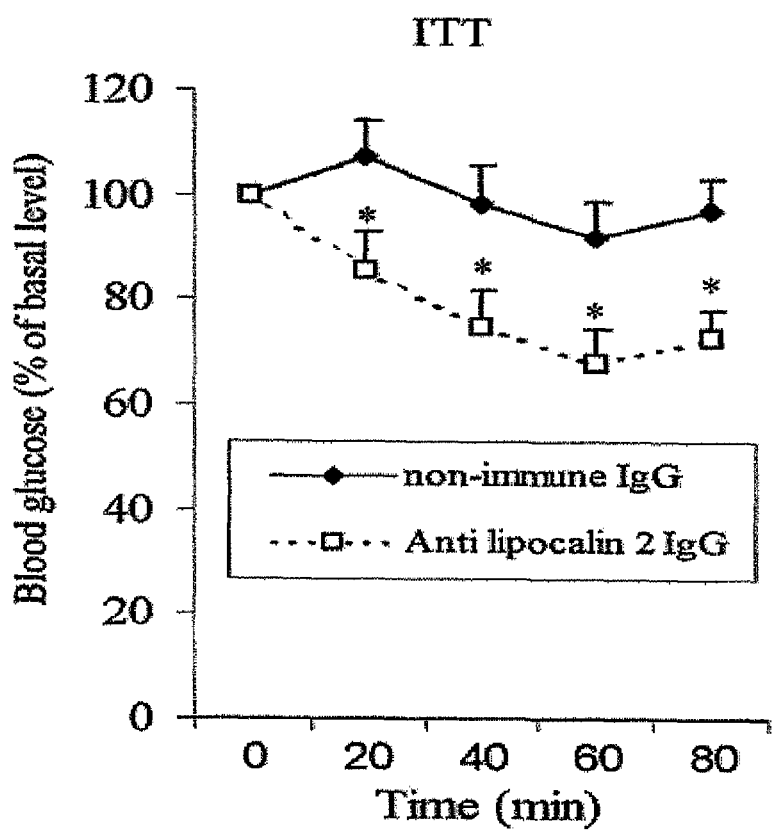

FIG. 7A is a line graph of blood glucose (mg/dL) versus time (minutes) in db/db obese/diabetic male mice (aged 10-12 week) treated with anti-lipocalin-2 IgG (□) or non-immune IgG (♦) for a period of 3 weeks. * P<0.05 versus mice treated with control IgG (n=6). FIG. 7B is a line graph a line graph of blood glucose (% of basal) versus time (min) in db/db obese/diabetic male mice (aged 10-12 week) treated with anti-lipocalin-2 IgG (□) or non-immune IgG (♦) for a period of 3 weeks

DETAILED DESCRIPTION OF THE INVENTION

I. Definitions

As used herein, the term "antibody" is meant to include both intact molecules as well as fragments thereof that include the antigen-binding site. These include Fab and F(ab')$_2$ fragments which lack the Fc fragment of an intact antibody.

The term "lipocalin-2" refers to the protein having 80%, 85%, 90%, 95%, 99% or 100% sequence identity to SEQ ID NO:1 or encoded by a nucleic acid having 80%, 85%, 90%, 95%, 99% or 100% sequence identity to (SEQ ID NO:2) (Accession Number NM_005564), and which hybridizes to SEQ ID:2 under stringent conditions.

The term "lipocalin-2 antagonist" refers to a substance that interferes, reduces, or inhibits the biological activity of lipocalin-2, preferably in a patient. The antagonist can also interfere, reduce, or inhibit the expression of lipocalin-2 in a patient, for example, by downregulation expression of a nucleic acid encoding lipocalin-2. Representative lipocalin-2 antagonist include, but are not limited to, PPARγ agonists, rosiglitazone, antibodies or fragments thereof that bind to at least one epitope on lipcalin-2, inhibitory nucleic acids such as siRNA, antisense RNA, microRNA, antisense DNA that hybridize to a sufficient portion of a nucleic acid encoding lipocalin-2 or a variant thereof to inhibit, reduce or interfere with expression of the nucleic acid.

The term "reference level" refers to a normalized level of lipocalin-2 determined from a population of subjects that are not obese and/or do not have an obesity-induced metabolic disorder.

As used herein, the term "polypeptide" refers to a chain of amino acids of any length, regardless of modification (e.g., phosphorylation or glycosylation).

As used herein, a "variant" polypeptide contains at least one amino acid sequence alteration as compared to the amino acid sequence of the corresponding wild-type polypeptide.

As used herein, an "amino acid sequence alteration" can be, for example, a substitution, a deletion, or an insertion of one or more amino acids.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

The terms "individual", "host", "subject", and "patient" are used interchangeably herein, and refer to a mammal, including, but not limited to, murines, simians, humans, mammalian farm animals, mammalian sport animals, and mammalian pets.

As used herein the term "effective amount" or "therapeutically effective amount" refers to the amount which is able to treat one or more symptoms of obesity or obesity-induced metabolic disorders, reverse the progression of one or more symptoms of obesity or obesity-induced metabolic disorders, halt the progression of one or more symptoms of obesity or obesity-induced metabolic disorders, or prevent the occurrence of one or more symptoms of obesity or obesity-induced metabolic disorders in a subject to whom the formulation is administered, as compared to a matched subject not receiving the compound. The actual effective amounts of compound can vary according to the specific compound or combination thereof being utilized, the particular composition formulated, the mode of administration, and the age, weight, condition of the individual, and severity of the symptoms or condition being treated.

The term "obesity-induced metabolic disorders" are disorders that are related to obesity or are caused by obesity. Representative obesity-induced metabolic disorders include, but are not limited to obesity, elevated serum triglyceride and decreased HDL-cholesterol, hyperinsulinemia, atherosclerosis, fasting glucose levels, Type 2 diabetes and other obesity-related inflammatory conditions.

The term "obesity" is typically defined as having a body mass index (BMI), expressed as weight/height$^2$ (BMI; kg/m$^2$) greater than or equal to 30.0. Overweight is classified as having a BMI of 25.0-29.9.

The term "treating" or "treatment" means reducing, inhibiting, or alleviating one or more symptoms related to obesity or an obesity-induced metabolic disorder.

II. Biomarkers for Obesity or Obesity-Induced Metabolic Disorders

A. Lipocalin-2

It has been discovered that lipocalin-2 or a variant thereof can be used as a biomarker to assess the propensity of a patient to develop obesity or obesity-induced metabolic disorders. Lipocalin-2, also known as 24p3 and neutrophil gelatinase-associated lipocalin (NGAL) (Kjeldsen, L., et al. *J Biol Chem.* 268:10425-10432 (1993)), is a 25 kDa secretory glycoprotein that was originally identified in mouse kidney cells and human neutrophil granules. It belongs to the lipocalin superfamily that includes over 20 small secretory proteins, such as RBP4, fatty acid binding proteins (FABP), major urinary proteins (MUP), apolipoprotein D (apoD) and prostaglandin D synthases (PGDS) et al. (Akerstrom, B., et al. *Biochim Biophys Acta.* 1482:1-8 (2000). The common feature of this protein family is their capacity to bind and transport small lipophilic substances, such as free fatty acids, retinoids, arachidonic acid and various steroids (Flower, D. R., *Biochem J.* 318:1-14. (1996). Although it has previously been reported that lipocalin-2 binds weakly with leukotriene $B_4$ and lipopolysaccharides (Bratt, T., et al., *Biochim Biophys Acta.* 1472:262-269 (1999)), its high affinity endogenous ligands remain to be identified.

In addition to neutrophils, lipocalin-2 is expressed in several other tissues, including liver, lung, kidney, adipocytes and macrophages (Liu, Q., and Nilsen-Hamilton, M. *J Biol. Chem.* 270:22565-22570 (1995); Kratchmarova, I., Kalume, D. E., et al. *Mol Cell Proteomics,* 1:213-222 (2002); Meheus, L. A., et al., *J Immunol.* 151:1535-1547 (1993). Several inflammatory stimuli, such as lipopolysaccharides and IL 1 beta, can markedly induce lipocalin-2 expression and secretion in these cells (Liu, Q., and Nilsen-Hamilton, M. *J Biol Chem.* 270:22565-22570 (1995); Jayaraman, A., et al., *Biotechnol Bioeng,* 91:502-515). Notably, the pro-inflammatory transcription factor NF-kappaB has been shown to transactivate lipocalin-2 expression through binding with a consensus motif within the promoter region of the lipocalin-2 gene (Fujino, R. S., Tet al., *Gene. Mol Endocrinol* 20:904-915 (2006), suggesting that this secretory protein might be involved in the inflammatory responses. Nevertheless, the roles of lipocalin-2 in obesity-associated inflammation and metabolic abnormalities have previously not been investigated.

B. Variants of Lipocalin-2

In certain embodiments, variants of lipocalin-2 or homologs thereof can be biomarkers of obesity or obesity-induced metabolic disorders, or can be therapeutic targets for these disorders. As used herein, a "variant" polypeptide contains at least one amino acid sequence alteration as compared to the amino acid sequence of the corresponding wild-type polypeptide, for example, the polypeptide according to MPLGLLWLGLALLGALHAQAQDSTSDLI-PAPPLSKVPLQQNFQDNQFQG KWYVVGLAGNAIL-REDKDPQKMYATIYELKEDKSYNVTSVLFRKKKC DYWIRTFVPGCQPGEFTLGNIKSYPGLT-SYLVRVVSTNYNQHAMVFFKK VSQNREYFKIT-LYGRTKELTSELKENFIRFSKSLGLPEN-HIVFPVPIDQCID G (SEQ ID NO:1). An amino acid sequence alteration can be, for example, a substitution, a deletion, or an insertion of one or more amino acids, preferably conservative substitutions A variant lipocalin-2 can have any combination of amino acid substitutions, deletions or insertions. In one embodiment, isolated lipocalin-2 variant polypeptides have an integer number of amino acid alterations such that their amino acid sequence shares at least 60, 70, 80, 85, 90, 95, 97, 98, 99, 99.5 or 100% identity with an amino acid sequence of (SEQ ID NO:1).

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.,* 48:443-453 (1970)); 2) BLOSSUM62 comparison matrix from Hentikoff and Hentikoff (*Proc. Natl. Acad. Sci. U.S.A.,* 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)* 100. For this calculation, alignment length includes internal gaps but does not include terminal gaps.

Amino acid substitutions in lipocalin-2 polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

It is understood that substitutions can be made using any amino acid or amino acid analog. For example, the substitutions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

III. Methods for Assessing the Propensity for or Diagnosing Obesity or Obesity-Induced Metabolic Disorders One method for assessing the risk or propensity to develop and/or the progression of obesity or obesity induced metabolic disorders such as glucose tolerance, insulin resistance and Type 2 diabetes in mammalian subjects is by determining the concentration of circulating lipocalin-2 in a subject and comparing the measured level to lipocalin-2 reference level Typically a sample is taken from a patient and the concentration of lipocalin-2 in the sample is determined. The sample can be blood, urine, saliva, cerebrospinal fluid, or tissue. If the concentration of the level of lipocalin-2 is higher than the concentration of the lipocalin-2 reference level, the risk or propensity of developing glucose tolerance, insulin resistance or Type 2 diabetes is greater for the patient than for a person having levels of lipocalin-2 that are lower than the reference level.

In certain embodiments, a positive reference level of lipocalin-2 can be obtained from adults confirmed as being obese or as having an obesity-induced metabolic disorder. A level of lipocalin-2 in the sample is within a statistically acceptable range, for example plus or minus 10% of the positive reference level, or is greater than the positive reference level and therefore indicative of obesity or an obesity-induced metabolic disorder in the subject.

The concentration of lipocalin-2 or a variant thereof can be determined using conventional techniques such as FACS, FACE, ELISA, Northern blotting and/or Western blotting. In a preferred embodiment, the amount of lipocalin-2 in a sample can be determined using immunological assays, for example ELISA assays or sandwich immunoassays. It will be appreciated that any means of quantifying lipocalin-2 or a variant thereof in a sample can be used. Representative techniques include, but are not limited to, immunoprecipitation, mass spectroscopy such as MALDI-TOF, electrophoresis, and chromatography including affinity chromatography.

Another method for diagnosing or aiding in the diagnosis of obesity, obesity-induced metabolic disorders, diabetes or insulin resistance in a subject includes obtaining a sample from the subject, preferably a blood sample and determining the lipocalin-2 level contained in the sample. The determined levels are compared to a reference level. In a preferred embodiment, obesity, hyperglycemia or insulin resistance is present if the lipocalin-2 level is higher than the reference level. In another preferred embodiment, the lipocalin-2 level in the blood sample is measured by an immunoassay, preferably a sandwich immunoassay. The results of this method can be used in combination with other tests to diagnosis obesity, diabetes or insulin resistance in a subject. For example, levels of serum lipids, BMI, the presence of plaques in arteries or veins, and insulin intolerance can be determined. These data combined with the determining the levels of lipocalin-2 can be used to assess the risk of developing or diagnosis the presence of obesity. Additional tests that can used in combination with the disclosed methods include detecting and or quantifying additional biomarkers including adiponectin, adipocyte fatty acid binding protein and high sensitivity reactive proteins.

IV. Methods of Treatment

Another embodiment provides a method for treating, preventing, or inhibiting at least one symptom associated with obesity, obesity-induced metabolic order such as insulin resistance, hyperglycemia, or type 2 diabetes by administering an effective amount of a lipocalin-2 antagonist to a subject to reduce, inhibit, or block lipocalin-2 activity or expression compared to subject who is not administered the lipocalin-2 antagonist.

Suitable lipocalin-2 antagonists include, but are not limited to antibodies or lipocalin-2 binding fragments thereof that bind to at least one epitope of a lipocalin-2 polypeptide. Additional lipocalin-2 antagonists include small molecules, for example organic molecules of about 500 daltons or less and PPARγ agonists. The antagonist can bind directly to lipocalin-2 polypeptide or lipocalin-2 nucleic acid and thereby inhibit or reduce the biological activity lipocalin-2 or the expression of lipocalin-2. Other lipocalin-2 antagonists include inhibitory nucleic acids that are complementary to and hybridize with a nucleic acid encoding lipocalin-2. Representative inhibitory nucleic acids include siRNA, miRNA, and antisense DNA.

In certain embodiments, the lipocalin-2 antagonist reduces serum levels of lipocalin-2 polypeptide in a patient by 10%, 20%, 30%, 40%, 50%, 60%, or 70% percent compared to patients not receiving the lipocalin-2 antagonist. The methods of treating insulin resistance, type 2 diabetes and other related complications by administering to a patient an effective amount of a composition can reduce the circulating levels of lipocalin-2 compared to a control.

V. Formulations

Compositions including a lipocalin-2 antagonist that are administered to an individual in need of treatment or prophylaxis of at least one symptom or manifestation (since disease can occur/progress in the absence of symptoms) of obesity or obesity-induced metabolic disorder are also provided. In one embodiment, the compositions are administered in an effective amount to inhibit gene expression of genes encoding lipocalin-2 or homologues thereof. Alternatively, a composition is administered in an amount to inhibit lipocalin-2 protein. In a preferred embodiment, the compositions are administered in an effective amount to inhibit or reduce lipid accumulation in skeletal muscle and liver, or reduce circulating levels of lipocalin-2 protein compared to a control.

The compounds are preferably employed for therapeutic uses in combination with a suitable pharmaceutical carrier. Such compositions include an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the lipocalin-2 antagonists described herein.

It is understood by one of ordinary skill in the art that antagonists of lipocalin-2 administered in vivo are taken up and distributed to cells and tissues (Huang, et al., *FEBS Lett.* 558(1-3):69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature,* 385:721-725 (1997). Small nucleic acids are readily taken up into T24 bladder carcinoma tissue culture cells (Ma, et al., *Antisense Nucleic Acid Drug Dev.* 8:415-426 (1998). siRNAs have been used for therapeutic silencing of an endogenous genes by systemic administration (Soutschek, et al., *Nature* 432, 173-178 (2004)).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers, proteins, lipids or liposomes for targeting to cells. Such systems are well known to those skilled in the art and may be optimized for use with the appropriate nucleic acid.

Various methods for nucleic acid delivery are described, for example in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative. The compositions may take such forms as.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, and nitrogen. For administration by inhalation, the compound are conveniently delivered in the form of an aerosol spray presentation from pressurized packs or a nebulizer, with the use of a suitable propellant. Alternatively, the formulations can be administered as dry powders by inhalation.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the compound is conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al. also described methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

The formulations described herein of the nucleic acids embrace fusions of the nucleic acids or modifications of the nucleic acids, wherein the nucleic acid is fused to another moiety or moieties, e.g., targeting moiety or another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, e.g., antibodies to adipocytes, immune cells, lung cells or any other preferred cell type, as well as receptor and ligands expressed on the preferred cell type.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the lipocalin-2 antagonist is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the lipcalin-2 antagonist. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

A. Methods of Administration

Compositions containing an effective amount of lipocalin-2 antagonist can be administered by a number of routes including, but not limited to: oral, intravenous, intraperitoneal, intramuscular, transdermal, subcutaneous, topical, sublingual, or rectal means. Such administration routes and appropriate formulations are generally known to those of skill in the art.

Administration of the formulations described herein may be accomplished by any acceptable method which allows the compounds, for small molecules, antibodies to lipocalin-2 or lipocalin-2-binding fragments thereof, or inhibitory nucleic acids, to reach its target. The particular mode selected will depend of course, upon factors such as the particular formulation, the severity of the state of the subject being treated, and the dosage required for therapeutic efficacy.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The nucleic acid may be delivered in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the lipocalin-2 antagonist over a certain time period, for example, hours, days, weeks, months or years. This may be accomplished, for example, by repeated administrations of a formulation or by a sustained or controlled release delivery system in which the antagonist is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

B. Effective Dosages

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the lipocalin-2 antagonist employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

Therapeutic compositions comprising one or more lipocalin-2 antagonists are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the lipocalin-2 antagonists at various concentrations, e.g., as applied to the mass and overall health of the individual. Administration can be accomplished via single or divided doses.

In vitro models can be used to determine the effective doses of the antagonists as a potential treatment for obesity or obesity-induced metabolic disorders. In determining the effective amount of the compound to be administered in the treatment or prophylaxis of disease the physician evaluates circulating plasma levels, formulation toxicities, and progression of the disease. For nucleic acid antagonists, the dose administered to a 70 kilogram individual is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined lipocalin-2 antagonists may be used together or sequentially.

VI. Screening

A method for screening substances useful for treating diseases such as obesity, obesity-induced metabolic disorders, hyperglycemia, glucose intolerance and insulin resistance have been developed. The method includes contacting a mammalian cell expressing a lipocalin-2 polypeptide or variant thereof with a test substance. The test substance is a substance believed to increase or decrease the biological activity or bioavailability of lipocalin-2. The method also includes determining whether lipocalin-2 polypeptide biological activity or expression is increased or decreased by the test substances. Such a determination can be made by detecting a phenotypic change in the cell or a detectable marker produced by the cell. In a preferred embodiment, the method includes selecting the test substance that causes a decrease in lipocalin-2 biological activity, expression, or bioavailability.

Methods for identifying modulators of the function, expression, or bioavailability of lipocalin-2 or nucleic acids encoding lipocalin-2 or homologues thereof utilize well known techniques and reagents. The modulator can increase or decrease lipocalin-2 function for example to reduce lipocalin-2 function in obesity or obesity-induced disorders such as insulin intolerance, type 2 diabetes, and coronary disease. Modulation of lipocalin-2 can be direct or indirect. Direct modulation refers to a physical interaction between the modulator and lipocalin-2 mRNA, protein, or DNA. Indirect modulation of lipocalin-2 can be accomplished when the modulator physically associates with a cofactor, second protein or second biological molecule that interacts with lipocalin-2 mRNA, DNA or protein either directly or indirectly. Additionally, indirect modulation includes modulators that affect the expression or the translation of RNA encoding lipocalin-2.

In some embodiments, the assays can include random screening of large libraries of test compounds. Alternatively, the assays may be used to focus on particular classes of compounds suspected of modulating the function or expression of lipocalin-2 or homologues thereof in cells, tissues, organs, or systems.

Assays can include determinations of lipocalin-2 mRNA expression, protein expression, or protein activity. Other assays can include determinations of lipocalin-2 nucleic acid transcription or translation, for example mRNA levels, mRNA stability, mRNA degradation, transcription rates, and translation rates.

In one embodiment, the identification of a lipocalin-2 modulator is based on the function of lipocalin-2 in the presence and absence of a test compound. The test compound or modulator can be any substance that alters or is believed to alter the function of lipocalin-2, in particular the function of lipocalin-2 in obesity and obesity-induced metabolic disorders. Typically, a modulator will be selected that reduces, eliminates, or inhibits lipocalin-2 activity under physiological conditions.

One exemplary method includes contacting lipocalin-2 or nucleic acid encoding lipocalin-2 with at least a first test compound, and assaying for an interaction between lipocalin-2 or the lipocalin-2 nucleic acid and the first test compound with an assay. The assaying can include determining lipocalin-2 activity.

Specific assay endpoints or interactions that may be measured in the disclosed embodiments include assaying for decrease in lipid accumulation and lipocalin-2 down or up regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as *C. elegans* and transgenic animals.

Other screening methods include using labeled lipocalin-2 protein or nucleic acid to identify a test compound. Lipocalin-2 can be labeled using standard labeling procedures that are well known and used in the art. Such labels include, but are not limited to, radioactive, fluorescent, biological and enzymatic tags.

Another embodiment provides a method for identifying a modulator of lipocalin-2 expression by determining the effect a test compound has on the expression of lipocalin-2 in cells. For example isolated cells or whole organisms expressing lipocalin-2 or both can be contacted with a test compound. Lipocalin-2 protein or nucleic acid expression can be determined by detecting lipocalin-2 protein expression or lipocalin-2 mRNA transcription or translation. Suitable cells for this assay include, but are not limited to, immortalized cell lines, primary cell culture, or cells engineered to express lipocalin-2, for example mammalian cells. Compounds that modulate the expression of lipocalin-2 in particular that reduce or inhibit the expression or bioavailability of lipocalin-2, can be selected. Alternatively, compounds that increase or enhance expression or activity of miRNA or siRNA specific for lipocalin-2 nucleic acid can be selected.

Another embodiment provides for in vitro assays for the identification of lipocalin-2 modulators or modulators of lipocalin-2 homologues. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule, for example a nucleic acid encoding lipocalin-2, in a specific fashion is strong evidence of a related biological effect. Such a molecule can bind to a lipocalin-2 nucleic acid and modulate expression of lipocalin-2, for example downregulate lipocalin-2. The binding of a molecule to a target may, in and of itself, be inhibitory, due to steric, allosteric or charge—charge interactions or may downregulate or inactivate lipocalin-2 protein or nucleic acid. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

In one embodiment, a transgenic cell having an expression vector for expressing lipocalin-2 can be generated by introducing the expression vector into the cell. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE, La Jolla, Calif.). Alternatively, bacterial cells such as *E. coli* LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including *C. elegans*, rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more test compounds are administered to an animal, and the ability of the test compound(s) to alter one or more characteristics, as compared to a similar animal not treated with the test compound(s), identifies a modulator. Other embodiments provide methods of screening for a test compound that modulates the function of lipocalin-2. In these embodiments, a representative method generally includes the steps of administering a test compound to the animal and determining the ability of the test compound to reduce one or more characteristics of aging, lifespan, or age-related disorder.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

The present invention is further understood by reference to the following non-limiting examples.

EXAMPLES

Example 1

Lipocalin-2 Production is Increased in db/db Diabetic/Obese Mice, But is Suppressed Following Treatment with the PPARγ Agonist Rosiglitazone Materials and Methods Animal Studies Male C57BL/6J and C57BKS db/db diabetic mice (The Jackson Laboratory) between 11- and 12-weeks old were used for this study. The mice were housed in a room under controlled temperature (23±1° C.), with free access to water and standard mouse chow. Rosiglitazone (GSK, UK) was administered into db/db mice by daily intra-gastric gavage (1 mg/kg body weight) for 2 weeks. All of the experiments were conducted under institutional guidelines for the humane treatment of laboratory animals.

Real Time Quantitative PCR

Total RNA was isolated from mouse livers epididymal adipose tissue and soleus muscle using the RNeasy kit (Qiagen). Subsequently, mRNA was reverse transcribed into cDNA using the oligo-dT primer (Roche). The relative gene abundance was quantified by Taqman real-time PCR using the pre-developed assay kits (Applied Biosystems, Foster city, Calif.). The reactions were performed on the ABI 7000 sequence detection system.

Results

Figure 1:
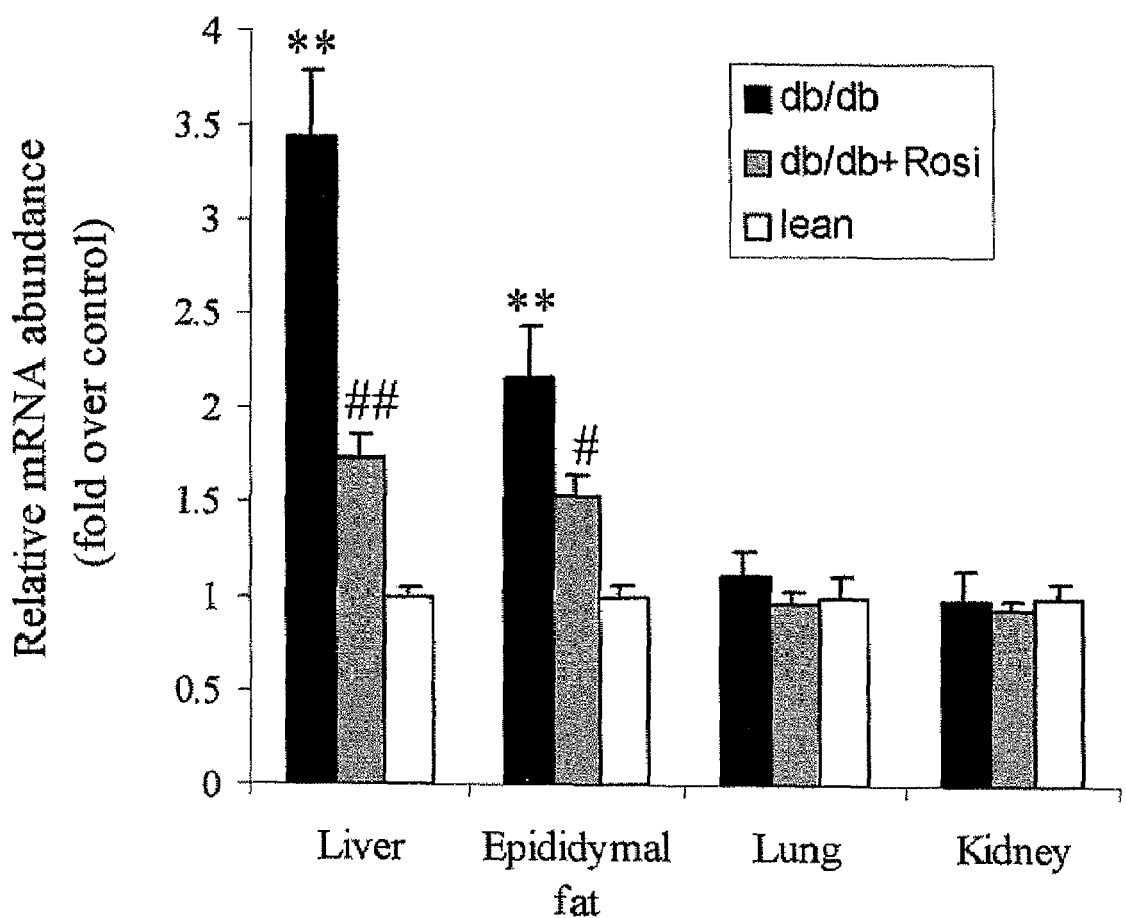
FIG. 1 shows a bar graph of the relative mRNA abundance (fold over control) of the lipocalin-2 gene in db/+heterozygous lean mice and db/db obese mice treated without or with rosiglitazone (rosi).

It has been discovered that the expression of a gene encoding lipocalin-2, a secretory protein with putative lipid-binding activity, was markedly induced in the liver tissue of db/db obese/diabetic mice. To explore the relevance of lipocalin-2 with obesity, real-time quantitative PCR analysis was used to further compare the expression profiles of lipocalin-2 between male db/db mice and their age- and sex-matched lean littermates in various tissues. In both liver and adipose tissue, the steady-state mRNA abundances of the lipocalin-2 gene in obese/diabetic db/db mice were substantially higher than those in their age- and sex-matched lean littermates (FIG. 1). In FIG. 1 total RNA was extracted from male lean mice or their age- and sex-matched db/db mice treated without or with rosiglitazone for 2 weeks. The steady state mRNA levels of lipocalin-2 in liver, epididymal fat pads, lung and kidney were quantified with real-time PCR and normalized against 18S RNA. ** $P<0.01$ versus lean control. # $P<0.05$, ## $P<0.01$ versus db/db mice without treatment. Treatment of db/db mice with rosiglitazone for a period of two weeks caused a marked reduction of lipocalin-2 mRNA expression in liver, and a modest but significant decrease in adipose tissue. On the other hand, the levels of lipocalin-2 mRNA in several other tissues, including lung, spleen and kidney, were comparable between the obese and lean mice.

Figure 2A:
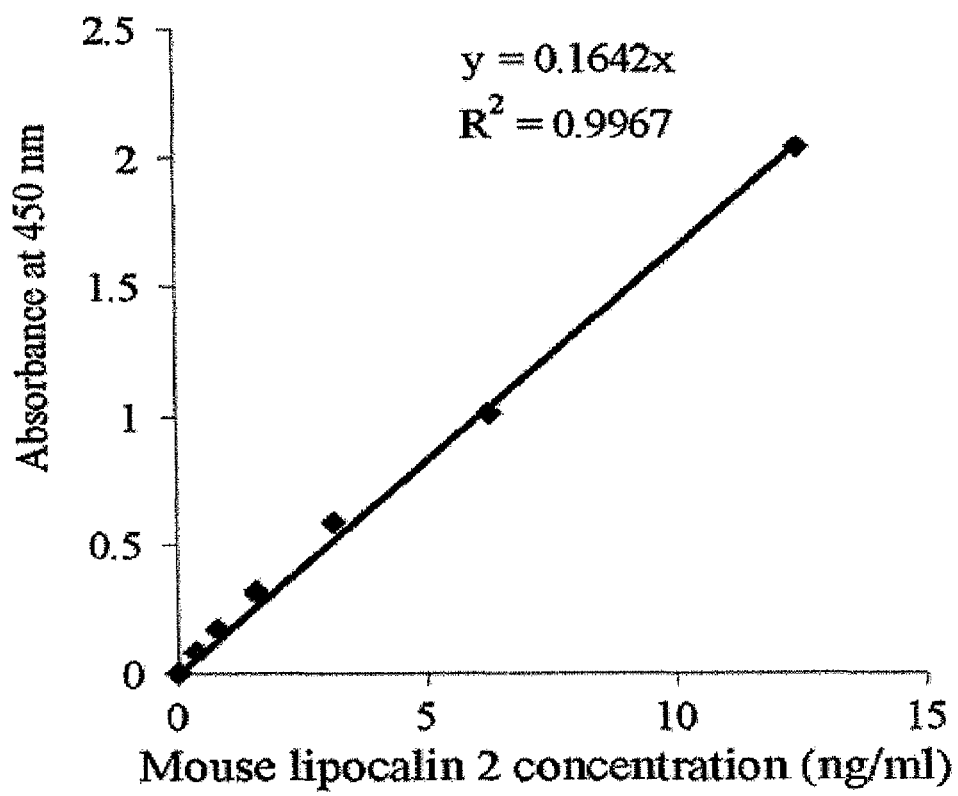
FIG. 2A depicts a line graph of absorbance (arbitrary units) versus mouse lipocalin-2 concentration (ng/ml) forming an ELISA standard curve generated using different concentrations of the recombinant protein.
Figure 2B:
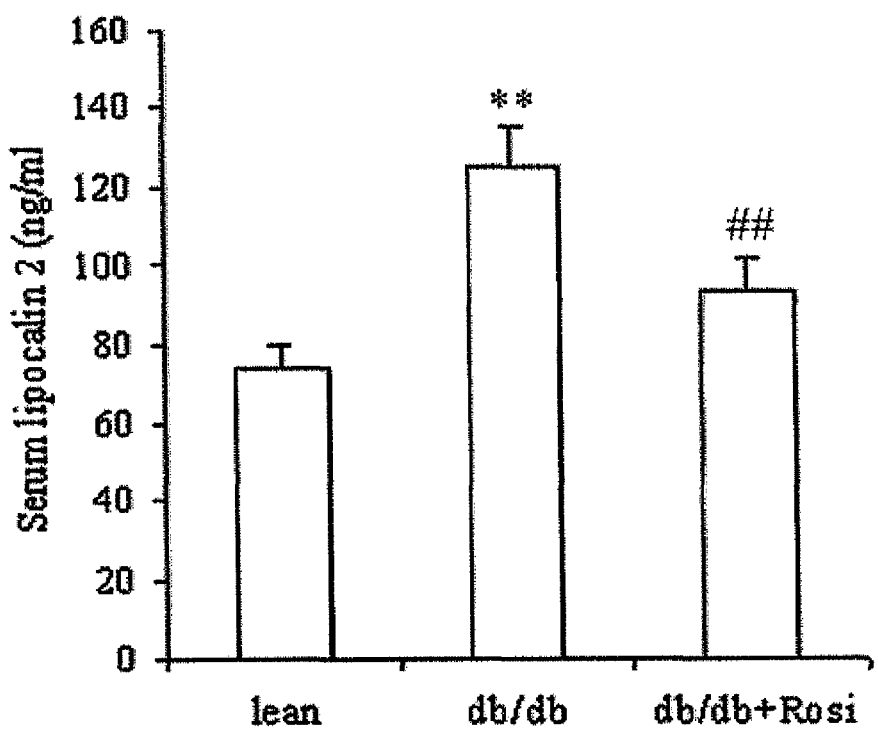
FIG. 2B is a bar graph of serum levels of lipocalin-2 in heterozygous lean mice and db/db mice treated without or with rosiglitazone ** P<0.01 versus lean control, ## P<0.01 versus db/db mice without treatment.

To investigate whether the altered mRNA expression in adipose tissue and liver leads to changes in circulating concentrations of lipocalin-2, a sandwich ELISA method for measuring this protein in serum samples was developed. To this end, a polyclonal antibody against mouse lipocalin-2, was developed using the recombinant protein as the antigen (FIGS. 2A-2B). 30 µg of proteins from bacterial lysate before (lane 1) or after (lane 2) induction with isopropylthio-β-d-galactoside (IPTG), or 5 µg of the purified protein (lane 3) was separated by 12% SDS-PAGE and stained with Commassie brilliant blue R250. The specificity of this antibody was validated by the fact that it could selectively immunoprecipitate recombinant lipocalin-2 from bacterial lysate (data not shown). The sandwich ELISA standard curve using recombinant murine lipocalin-2 yielded a consistent $r^2$ value>0.985. This analysis revealed that circulating concentrations of lipocalin-2 in db/db mice were significantly higher than those of their lean littermates. On the other hand, rosiglitazone treatment decreased circulating lipocalin-2 concentrations in db/db mice.

Example 2

Evaluation of Serum Levels of Lipocalin-2 in Obesity, Obesity-Related Anthropometric and Biochemical Variables in Subjects

Materials and Methods

Antibody Production and Development of Sandwich ELISA for Quantification of Murine and Human Lipocalin-2

Polyclonal antibodies against the recombinant human or murine lipocalin-2 were generated in New Zealand female rabbits as described by Xu, A. et al. *Proc Natl Acad Sci USA* 102:6086-6091 (2005). Anti-human or murine lipocalin-2 IgG was purified from the immunized rabbit serum using protein A/G beads, followed by the affinity chromatography using their respective antigens as the ligands.

The affinity-purified anti-human or anti-murine lipocalin-2 IgG was biotinylated with a kit from Pierce and used as the detection antibodies. The unlabeled anti-human or anti-murine lipocalin-2 IgG was used for coating a 96-well microtiter plate overnight at 4° C. Human or mouse serum was diluted (1:50) into PBS, and 100 µl of the diluted samples or recombinant standards were applied to each well and incubated at 37° C. for 1 h. The plates were washed three times and then incubated with 100 µl of the detection antibody for another 2 h. After washing for another three times with PBS, the wells were incubated with streptavidin-conjugated horseradish peroxidase for 1 h and subsequently reacted with tetramethylbenzidine reagent for 15 min. A total of 100 µl of 2 M $H_2SO_4$ was added to each well to stop the reaction, and the absorbance at 450 nm was measured. The intra- and inter-assay coefficients of variance were determined by measuring five serum samples in a total of six independent assays with duplicate determinations.

Human Subjects

Serum samples from a total of 229 human subjects collected from the previous cross-sectional Hong Kong Cardiovascular Risk Factor Prevalence Study (CRISP) (Tan, K. C., et al. *Diabetes Care* 26:2323-2328 (2003)). were used for measurement of lipocalin-2 levels. The clinical characteristics of these subjects were described in our previous reports (id). The subjects were stratified into lean (BMI<25 kg/m²), overweight (25-29.9 kg/m²) and obese (BMI>30 kg/m²) groups according to the WHO guidelines.

Results

To investigate the relationship between lipocalin-2 and obesity in human subjects, an in-house immunoassay for measurement of human lipocalin-2 was developed. The assay is highly specific to human lipocalin-2 with no detectable cross-reactivity to several other human adipokines and cytokines, including adiponectin, leptin, resistin, TNFα, C-reactive protein, IL 6 and other lipocalin family members, including RBP4 and adipocyte fatty acid binding protein (data not shown). The intra- and inter-assay coefficients of variance were 3.8-6.0% and 3.1-5.2% respectively. This analysis showed that the circulating concentrations of lipocalin-2 ranges from 20.9 to 182.5 ng/ml among 229 human subjects studied. Serum lipocalin-2 concentrations in male were significantly higher than those in female in both obese and lean groups, as shown in Table 1.

TABLE 1

Comparison of serum lipocalin-2 levels (ng/ml) between lean and obese subjects.

|  | Obese | Lean |
| --- | --- | --- |
| Female | 92.9 ± 46.6 | 64.1 ± 35.9* |
|  | (n = 25) | (n = 47) |
| Male | 117.7 ± 48.7# | 76.4 ± 38.7**,# |
|  | (n = 24) | (n = 55) |
| Total | 105.0 ± 48.8 | 70.7 ± 37.8** |
|  | (n = 49) | (n = 102) |

*$P < 0.05$,
**$P < 0.001$ versus obese group;
$P < 0.05$ versus female group.

Notably, the circulating levels of lipocalin-2 in obese subjects were significantly higher than those in lean individuals, and this difference was significant in both genders. A strong positive correlation was observed between serum lipocalin levels and BMI as shown in Table 2.

TABLE 2

Clinical characteristics of 229 subjects and correlation
between serum LCN2 levels and several study variables

| Parameter | Value | $r^a$ | $p^a$ | $r^b$ | $p^b$ |
|---|---|---|---|---|---|
| BMI (kg/m$^2$) | 27.1 ± 6.4 | 0.394 | <0.001 | — | — |
| WC (cm) | 87.3 ± 15 | 0.404 | <0.001 | 0.111 | 0.085 |
| Fat percentage (%) | 31.5 ± 10.0 | 0.296 | 0.001 | 0.184 | 0.033 |
| WHR | 0.9 ± 0.1 | 0.257 | <0.001 | 0.052 | 0.423 |
| Systolic blood pressure (mmHg) | 129.6 ± 21.2 | 0.154 | 0.017 | 0.001 | 0.990 |
| Diastolic blood pressure (mmHg) | 77.2 ± 11.0 | 0.031 | 0.637 | −0.088 | 0.173 |
| triglycerides (mmol/l) | 1.6 ± 1.1 | 0.151 | 0.019 | 0.074 | 0.255 |
| LDL-cholesterol (mmol/l) | 3.3 ± 0.8 | −0.082 | 0.216 | −0.075 | 0.259 |
| HDL-cholesterol (mmol/l) | 1.2 ± 0.3 | −0.200 | 0.002 | −0.104 | 0.111 |
| Fasting insulin (mIU/l) | 11.2 ± 7.3 | 0.269 | <0.001 | 0.069 | 0.286 |
| Fasting glucose (mmol/l) | 6.3 ± 2.2 | 0.148 | 0.021 | 0.142 | 0.027 |
| 2 h postprandial glucose (mmol/l) | 8.1 ± 3.9 | −0.063 | 0.451 | −0.045 | 0.587 |
| HOMA IR | 3.1 ± 2.3 | 0.305 | <0.001 | 0.145 | 0.025 |

After adjustment for sex and age, serum levels of lipocalin-2 were positively correlated with waist-to-hip ratio; waist circumference; fat percentage; systolic blood pressure; fasting serum concentrations of insulin; triglycerides; and fasting glucose levels; and the insulin resistance index by homeostasis model assessment (HOMA-IR) (Matthews, D. R., et al. *Diabetologia* 28:412-419 (1985)). On the other hand, serum levels of lipocalin-2 were negatively correlated with fasting serum concentrations of HDL-cholesterol. Notably, the positive correlations of serum lipocalin-2 with fasting glucose and HOMA-IR were still significant even after adjustment for BMI, suggesting that lipocalin-2 might be an independent risk factor for insulin resistance and/or diabetes in humans.

Example 3

Rosiglitazone Treatment Decreases Serum Lipocalin-2 Levels in T2DM Patients

Materials and Methods

The effect of rosiglitazone on serum levels of lipocalin-2 was investigated in 32 T2DM patients (see Example 2) treated with this drug (4 mg twice daily) for 8 weeks.

Results

As shown in Table 3, this treatment significantly decreased fasting blood glucose levels and insulin concentrations. Notably, these changes were associated with a reduction of circulating lipocalin-2 concentrations, suggesting that suppression of lipocalin-2 production might partly account for the insulin-sensitizing activities of rosiglitazone in human subjects

TABLE 3

Effects of rosiglitazone treatment on serum levels
of lipocalin-2 and several other metabolic parameters
in 32 T2DM patients (21 male and 11 female)

| | Baseline | 8 weeks |
|---|---|---|
| Body Mass Index (Kg/m$^2$) | 25.4 ± 3.6 | 25.5 ± 3.6 |
| Fasting Glucose (mM) | 8.7 ± 1.5 | 6.8 ± 1.2** |
| Fasting Insulin ((mIU/l)) | 10.2 ± 5.0 | 7.9 ± 3.5* |
| HOMA-IR | 4.0 ± 2.2 | 2.4 ± 1.2** |
| Lipocalin-2 (ng/ml) | 83.0 ± 29.7 | 61.9 ± 25.9** |

*$P < 0.05$;
**$P < 0.01$ versus baseline

Example 4

Chronic Treatment of Lipocalin-2 Induces Glucose Intolerance and Insulin Resistance, and Increases Lipid Accumulation in Skeletal Muscle and Liver Tissue Materials and Methods Measurement of Blood Parameters, Intraperitoneal Glucose Tolerance Test (ipGTT) and Insulin Tolerance Test (ITT)

Fasting (16 hr) plasma glucose levels and triglyceride (TG) concentrations were measured by using a Glucose (GO) assay kit (Sigma) and Triglyceride GPO reagent (Pointe Scientific Inc., Lincoln Park, Mich., USA) respectively. Fasting serum insulin concentrations were quantified by using the commercial ELISA kits from Mercodia AB (Uppsala, Sweden). Serum total cholesterol and free fatty acids (FFAs) were analyzed by using the kits from Wako (Richmond, Va., USA) and Roche Diagnostics respectively. TG contents in liver and soleus muscle were analyzed as described elsewhere (Ellis, B. A et al., *Am J Physiol Endocrinol Metab.* 279:E554-560 (2000); Xu, A., et al. *J Clin Invest* 112:91-100 (2003)).

For ipGTT, overnight fasted mice (16 hr) were given a glucose load by intraperitoneal injection (1 g glucose/kg body weight). For ITT, mice were starved for 6 h, and then intraperitonally injected with insulin (1 U/kg body weight). Plasma glucose levels were measured at different time points as indicated.

Results

To evaluate the effect of lipocalin-2 on glucose homeostasis and insulin sensitivity, normal C57 mice were treated with murine lipocalin-2 by intraperitoneal injection of the recombinant protein (5 mg protein/kg body weight, twice a day at 12 hr intervals). This treatment resulted in a daily average of serum lipocalin-2 levels about 2.2-3.5 folds higher than that of the endogenous protein. Chronic administration of recombinant lipocalin-2 for a period of 4 weeks had no obvious effects on body weight gain, food intake, and fasting serum levels of TG, cholesterol and free fatty acid, as shown in Table 4.

TABLE 4

Body weight, food intake and metabolic parameters in C57 mice treated with lipocalin-2 or vehicle control.

|  | Vehicle (n = 6) | Lipocalin-2 (n = 5) |
|---|---|---|
| Body weight gains over 4 weeks (g) | 2.18 ± 0.17 | 2.63 ± 0.19 |
| Daily average food intake (g) | 1.64 ± 0.18 | 1.75 ± 0.20 |
| Plasma glucose (mg/dL) | 109.4 ± 9.8 | 137.4 ± 11.6* |
| Plasma insulin (ng/ml) | 1.1 ± 0.03 | 1.5 ± 0.04* |
| Serum TG (mg/dL) | 87.3 ± 7.2 | 93.9 ± 8.9 |
| Serum total cholesterol (mg/dL) | 93.6 ± 7.6 | 101.4 ± 8.8 |
| Serum FFAs (mmol/L) | 0.61 ± 0.05 | 0.72 ± 0.08 |
| Serum adiponectin (μg/ml) | 11.1 ± 2.4 | 7.9 ± 1.8* |
| TG contents in liver (mg/g tissue) | 5.6 ± 0.5 | 6.9 ± 0.8* |
| TG contents in muscle (mg/g tissue) | 4.7 ± 0.4 | 7.3 ± 0.8** |

*$P < 0.05$,
**$P < 0.01$ versus vehicle-treated mice.

Figure 3A:
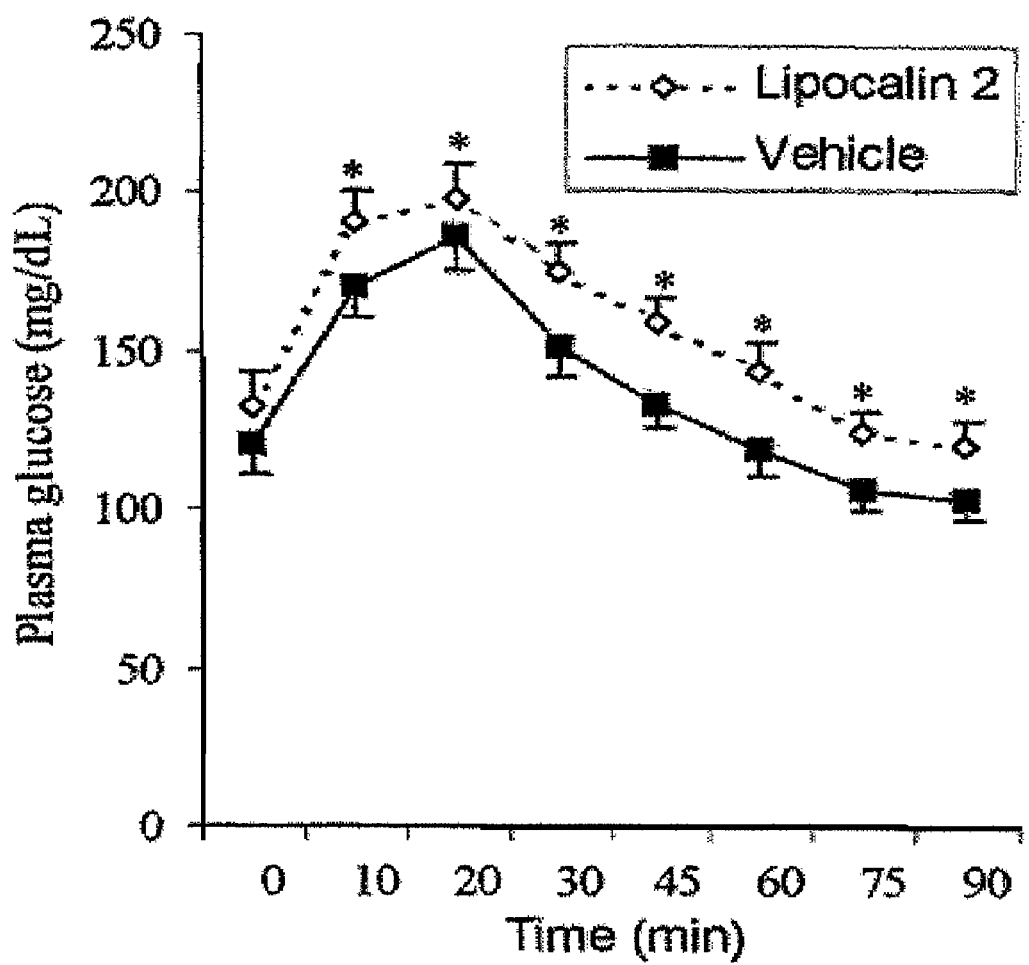
FIGS. 3A-3B show line graphs of plasma glucose (mg/dl) over time.
Figure 3B:
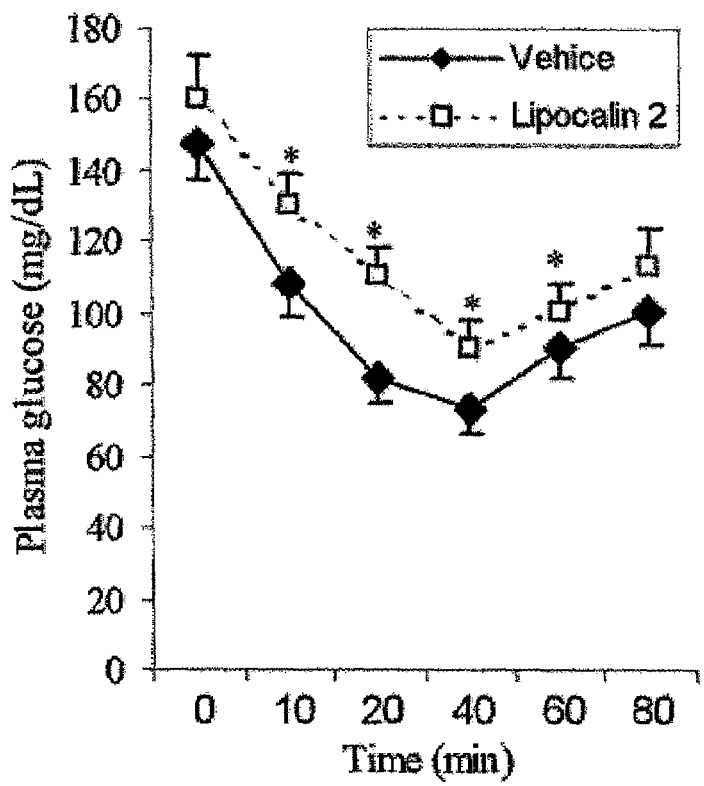

This treatment led to a significant elevation in fasting plasma glucose and insulin concentrations, and caused a significant reduction in circulating levels of total adiponectin. Notably, in lipocalin-2-treated mice, the triglyceride contents were markedly increased in skeletal muscle, and were modestly elevated in liver. GTT and ITT experiments demonstrated that long-term treatment with lipocalin-2 induced glucose intolerance and decreased insulin sensitivity, as seen in FIGS. 3A-3B.

Example 5

Long-Term Administration with Lipocalin-2 Alters the Expression of Several Key Genes Involved in Glucose and Lipid Metabolism Materials and Methods Expression and Purification of Recombinant Murine and Human Lipocalin-2 cDNA obtained from 3T3-L1 adipocytes were used as templates for amplification of the murine lipocalin-2 gene using 5'-AGTAGGATCCCAGGACTCAACTCAGAACTTG3' (SEQ ID NO:3) and 5'-AGTACTCGAGTCAGTTGTCAAT-GCATTGGTC3' (SEQ ID NO:4) as upstream and downstream primers respectively. The amplified PCR products were double-digested by the restriction enzymes BamHI and XhoI, and subsequently subcloned into the pPROEX-HTb vector (Invitrogen), resulting in an expression vector pPRO-His-mLCN2, which encodes $NH_2$-terminal $His_6$ tagged murine lipocalin-2 with 181 amino acid residues starting immediately after secretory signal peptide. The gene encoding human lipocalin-2 was amplified from cDNA derived from human HepG2 cells, using 5'-TGCAGGATCCCAG-GACTCCACCTCAGACC3' (SEQ ID NO:5) and 5'-TAGC-CTCGAGTCAGCCGTCGATACACTGGTCG3' (SEQ ID NO:6) as sense and anti-sense primers respectively. Following digestion with BamHI and XhoI, the PCR fragments were cloned into pPROEX-HTb vector to generate the construct pPRO-His-hLCN2 for prokaryotic expression of $NH_2$ terminal $His_6$ tagged human lipocalin-2 with secretory signal peptide removed. The inserted human or murine lipocalin-2 cDNA was verified by DNA sequencing.

The expression of His-tagged murine or human lipocalin-2 in BL21 cells was induced by the addition of 0.5 mM of isopropyl-β-D-thiogalactopyranoside to the growth medium. The recombinant proteins were purified from the bacterial lysates using the $Ni^{2+}$-nitrilotriacetic acid-agarose column as we previously described (Wang, Y., et al. *J Biol Chem*, 277: 19521-19529 (2002). Following purification, the $NH_2$-terminal $His_6$ tag was removed by cleavage with recombinant TEV protease, and the endotoxin was removed by using the Detoxi-gel Endotoxin-removal kit (Pierce). The purity of the protein was confirmed by SDS-PAGE and FPLC analysis.

Results

Figure 4A:
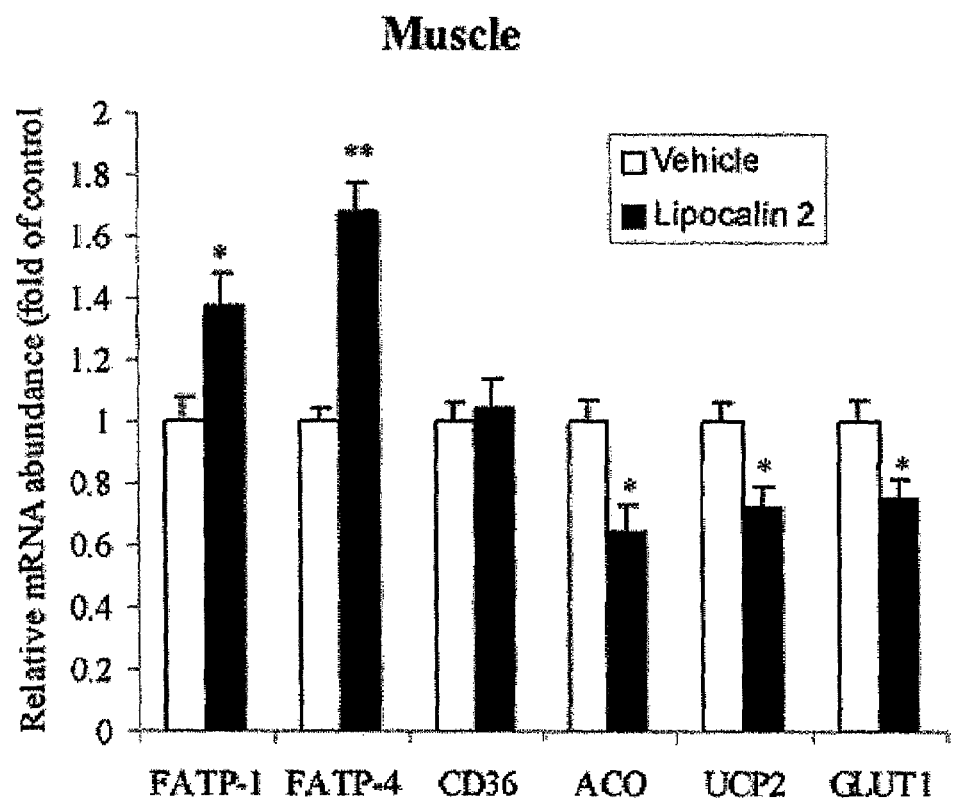
FIG. 4A is a bar graph of relative mRNA abundance (arbitrary units) for fatty acid transport protein 1 (FATP-1), fatty acid transport protein 4 (FATP-4), CD36, acyl-CoA oxidase (ACO), uncoupling protein-2 (UCP2), and GLUT1, after normalization against 18S RNA. * P<0.05; ** P<0.01 versus vehicle-treated mice.
Figure 4B:
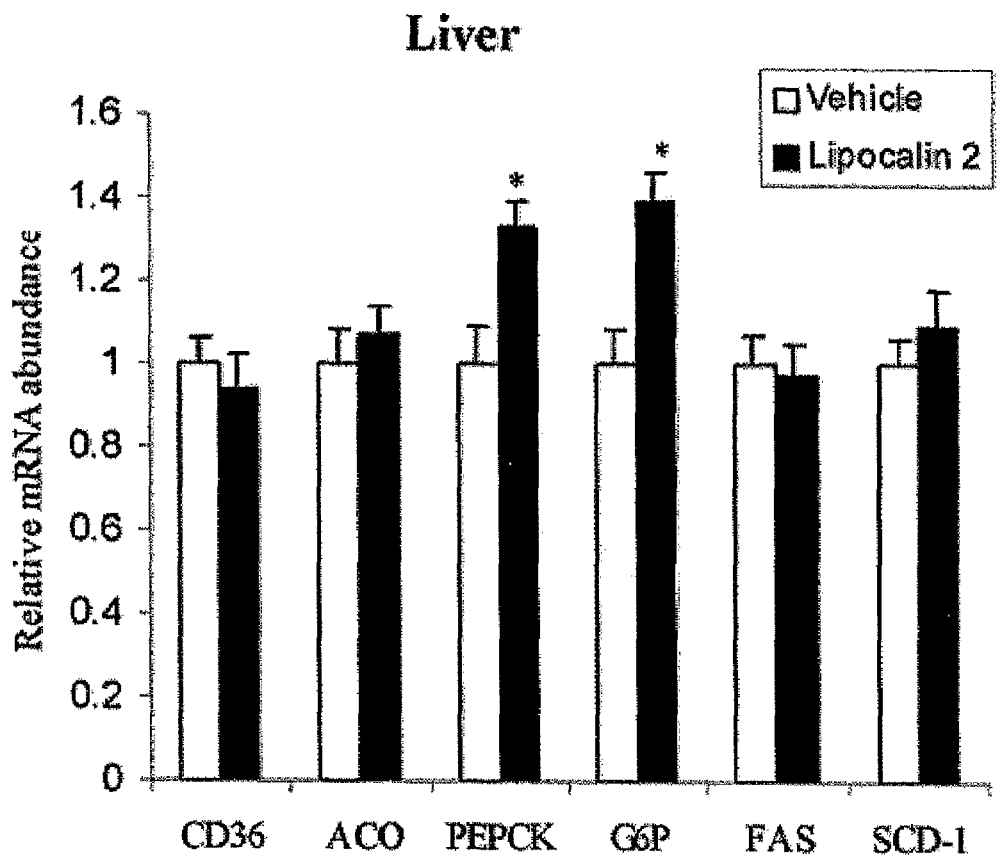
FIG. 4B is a bar graph of relative mRNA abundance (arbitrary units) for acyl-CoA oxidase (ACO), phosphoenolpyruvate carboxykinase (PEPCK), glucose-6-phosphatase (G6P), fatty acid synthase (FAS), stearoyl-CoA desaturease (SCD-1), after normalization against 18S RNA. * P<0.05; ** P<0.01 versus vehicle-treated mice.

The effects of lipocalin-2 on mRNA expression of several genes involved in glucose and lipid metabolism in skeletal muscle and liver were investigated (FIGS. 4A-4B). In skeletal muscle, treatment with lipocalin-2 significantly increased the steady-state mRNA levels of fatty acid transport protein 1 and 4 (FATP-1 and 4), but inhibited the expression of acyl-CoA oxidase and uncoupling protein 2 (UCP2), the two genes critically involved in energy dissipation. It also decreased the expression of GLUT1, a glucose transporter involved in basal glucose uptake. On the other hand, lipocalin-2 did not affect the expression of GLUT4, acetyl CoA carboxylase (ACO) and several other fatty acid transport proteins (FATP2, 3 and 5, and CD36).

In the liver tissue, lipocalin-2 induced a modest, but significant increase in expression of phosphoenolpyruvate carboxylase (PEPCK) and glucose-6-phosphatase (G6P), the two genes involved in gluconeogenesis. However, treatment with this protein did not modulate the expression of several genes involved in fatty acid transport, synthesis and oxidation (FIGS. 4A-4B).

Example 6

Prolonged Incubation with Lipocalin-2 Increases Intracellular Triglyceride Accumulation and Inhibits Basal Glucose Uptake in L6 Myotubes Materials and Methods Cell Culture Rat L6 skeletal myoblasts were grown in α-minimum essential medium (αMEM) containing 10% (v/v) FBS and 1% antibiotic solution (100 units/ml penicillin, 100 μg/ml streptomycin, 250 ng/ml amphotericin B) in a humidified atmosphere of 95% air and 5% $CO_2$ at 37° C. For differentiation to myotubes, cells were cultured in αMEM containing 2% (v/v) FBS for 5-7 days.

Measurement of Fatty Acid Uptake

[$^3$H]-palmitic acid (Amersham, Quebec, Canada) was used to determine fatty acid uptake as previously described (Bastie, C. C., et al. *Diabetes*, 53:2209-2216 (2004)). with slight modifications. Briefly, at day 5, cells were incubated with various concentrations of lipocalin-2 for 48 h, and subsequently serum-starved for the final 4 h in the continued presence of lipocalin-2. After treatments, culture medium was removed and cells washed twice with wash buffer (140 mM NaCl, 20 mM HEPES-Na, 2.5 mM $MgSO_4$, 1 mM $CaCl_2$, 5 mM KCl pH 7.4, 0.1% defatted albumin) and once with HEPES buffer. Cells were subsequently incubated with transport solution (10 μM defatted albumin, 0.5 μCi/ml [$^3$H]-palmitic acid; FA:BSA ratio=2) for 1 minute at room temperature. Then the reaction was stopped by washing with pre-cold stop buffer (140 mM NaCl, 20 mM HEPES-Na, 2.5 mM $MgSO_4$, 1 mM $CaCl_2$, 5 mM KCl pH 7.4) Non-specific uptake was measured in the presence of excess palmitate (2 mM) and subtracted from all other values. Cells were then lysed with 1 M KOH and aliquots were transferred to scintillation vials for $^3$H radioactivity counting.

Measurement of Glucose Uptake

Cells were incubated with various concentration of lipocalin-2 for 20 h, subsequently serum-starved in the continued presence of lipocalin-2 for the final 4 h in 24-well plates prior to further treatment. Cells were then washed twice with PBS and treated with insulin or vehicle for 15 min. After treatments, glucose uptake was determined. Briefly, cells were incubated in transport solution (140 mM NaCl, 20 mM HEPES-Na, 2.5 mM MgSO$_4$, 1 mM CaCl$_2$, 5 mM KCl and 0.5 μCi/ml 2-deoxy-D-[$^3$H]glucose, pH 7.4) for 5 min at room temperature. Nonspecific uptake was measured in the presence of cytochalasin B (10 μM). Cells were then lysed with 1 M KOH, and aliquots were transferred to scintillation vials for $^3$H radioactivity counting.

Results

Figure 5A:
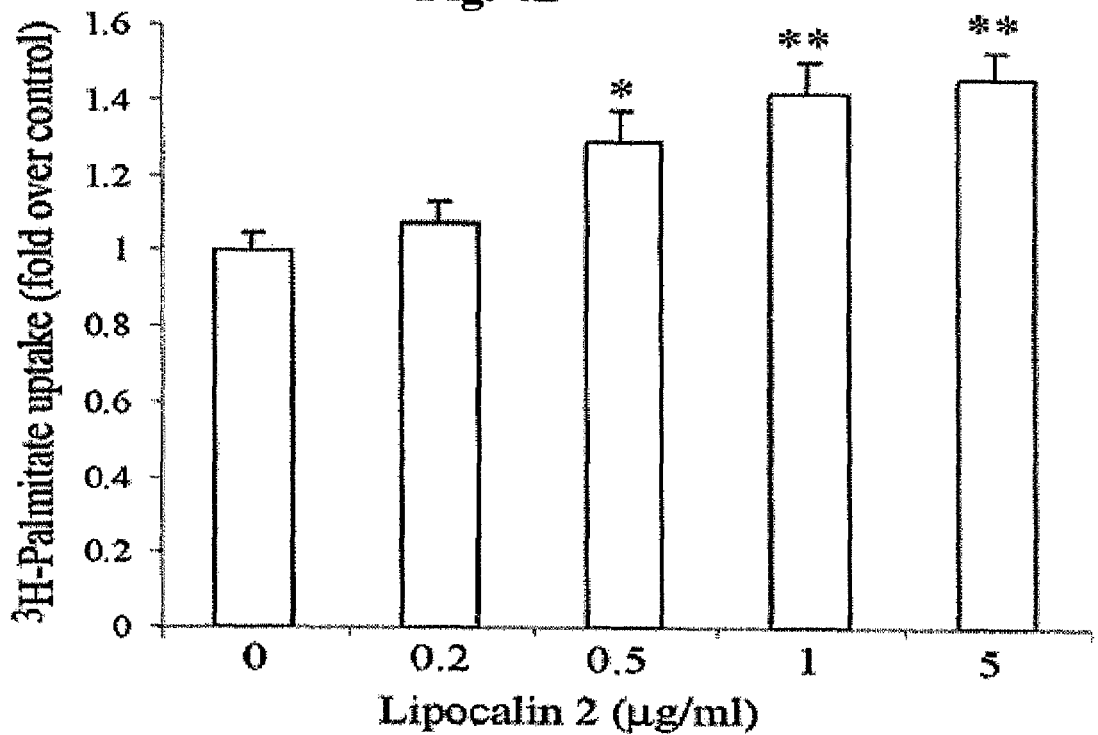
FIG. 5A is a bar graph of mRNA $^3$H-palmitate uptake (fold over control) in differentiated L6 myotubes treated with the indicated concentrations of lipocalin-2 or vehicle for 48 hr.
Figure 5B:
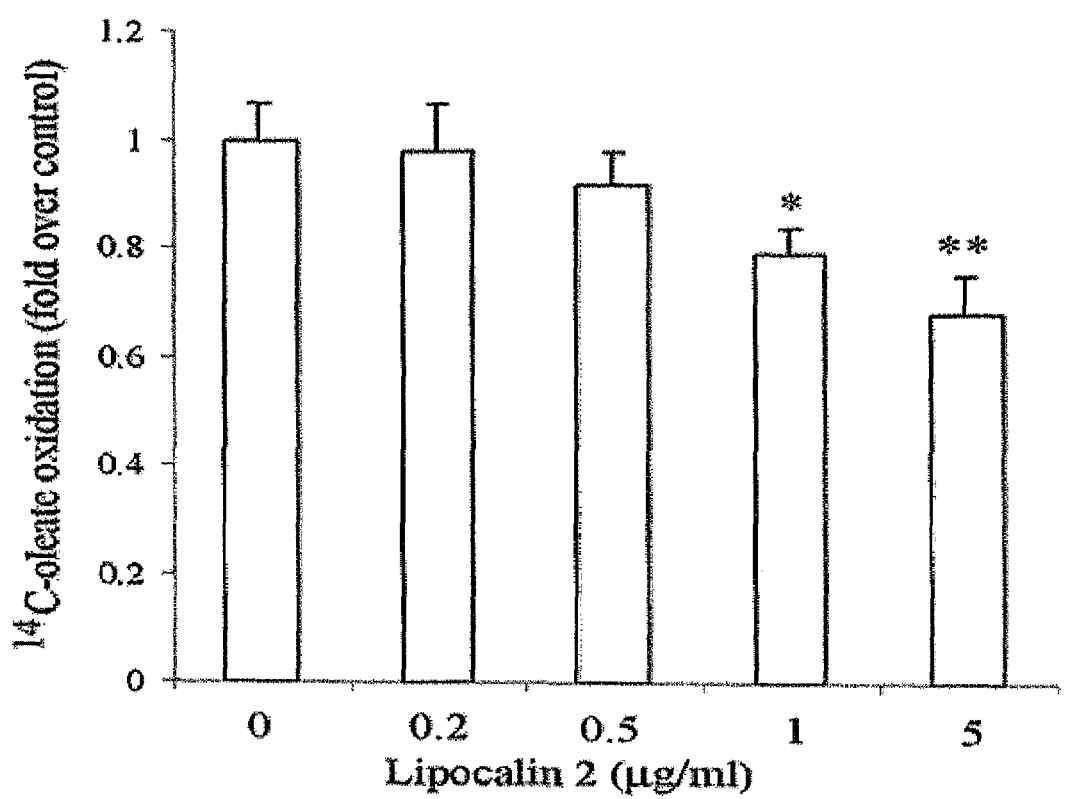
FIG. 5B is a bar graph of $^{14}$C-oleate oxidation (fold over control) in differentiated L6 myotubes treated with the indicated concentrations of lipocalin-2 or vehicle for 48 hr. Fatty acid oxidation was quantified by the production of $^{14}$CO$_2$ from [1-$^{14}$C]oleate.

Acute treatment with lipocalin-2 (within 2 hr) (produced as in Example 5) had no obvious effects on basal and insulin-stimulated glucose uptake, or fatty acid uptake and oxidation in L6 myotubes (data not shown). Prolonged incubation of L6 myotubes with lipocalin-2 (24 h and 48 h) caused a significant increase in fatty acid uptake, but a decrease in the rate of fatty acid oxidation (FIGS. 5A-5B). As a consequence, triglyceride accumulation in L6 myotubes at 72 hr following lipocalin-2 treatment was increased by 1.51±0.58 folds when compared with that in untreated cells (n=4, p<0.05).

At 48 hr after lipocalin-2 treatment, basal glucose uptake was significantly decreased (FIG. 6), a finding consistent with in vivo data showing decreased GLUT1 expression in lipocalin-2 treated mice (FIGS. 4A-4B). The magnitude of insulin-stimulated increase in glucose uptake in lipocalin-2-treated cells was slightly lower than that in untreated cells, although it was not statistically significant.

Example 7

Neutralization of Circulating Lipocalin-2 Alleviates Hyperglycemia and Insulin Resistance Associated with db/db Obese/Diabetic Mice Materials and Methods Whether the elevated serum lipocalin-2 in db/db mice is causally related to obesity-related metabolic abnormalities was investigated by administering anti-lipocalin-2 polyclonal antibodies (see Example 1) to neutralize its actions. To this end, db/db male mice were treated with affinity-purified anti lipocalin-2 IgG or rabbit non-immune IgG (as a control) by daily intraperitoneal injection (10 mg/kg body weight) for a period of 3 weeks.

Statistical Analysis

All the statistical calculations were performed with the SPSS 11.5 statistical software package (SPSS Inc). Pearson's correlation coefficient was used to establish the association between serum lipocalin-2 levels and various anthropometric and biochemical parameters. Comparison between groups was performed using Student's unpaired t-test, or when involving more than 2 groups, ANOVA followed by post hoc analysis employing Bonferroni corrections. In all statistical comparisons, a P value<0.05 was used to indicate a significant difference.

Results

Treatment of mice with anti-lipocalin-2 IgG had no obvious effect on body weight gain and food intake (data not shown). This treatment caused a significant alleviation of hyperglycemia and hyperinsulinemia, and a marked reduction of triglyceride accumulation in both skeletal muscle and liver when compared to those treated with non-immune IgG (Table 5). Furthermore, mice treated with anti-lipocalin-2 IgG showed significantly improved glucose tolerance and insulin sensitivity as determined by glucose and insulin tolerance tests (FIGS. 7A-7B). Taken together, these data indicate that elevated lipocalin-2 is involved in mediating obesity-related peripheral lipid accumulation, insulin resistance and hyperglycemia in db/db mice.

TABLE 5

Metabolic parameters of db/db mice after treatment with anti-murine lipocalin-2 IgG or rabbit non-immune IgG (n = 6 in each group)

| | Nonimmune IgG (control) | IgG against murine lipocalin-2 |
|---|---|---|
| Plasma glucose (mg/dL) | 261.8 ± 16.9 | 203.7 ± 11.6* |
| Plasma insulin (ng/ml) | 13.9 ± 0.7 | 10.2 ± 0.6* |
| Serum TG (mg/dL) | 208.4 ± 15.2 | 193.8 ± 10.6 |
| TG contents in liver (mg/g tissue) | 17.2 ± 1.3 | 12.9 ± 0.7* |
| TG contents in muscle (mg/g tissue) | 11.9 ± 0.6 | 7.4 ± 0.3** |
| Serum total cholesterol (mg/dL) | 149.7 ± 10.5 | 146.8 ± 9.3 |
| Serum FFAs (mmol/L) | 1.21 ± 0.07 | 1.08 ± 0.04 |
| Serum adiponectin (μg/ml) | 12.7 ± 2.9 | 16.9 ± 4.6 |

*$p < 0.05$;
**$p < 0.01$ versus control group

SUMMARY

Although lipocalin-2 has been identified for over a decade, the physiological functions of this protein remain poorly understood. Previous studies have been focusing on the role of this protein in the innate immune response to bacterial infection (Flo, T. H., et al. Nature, 432:917-921 (2004)). and in apoptosis (Devireddy, L. R., et al., Science, 293:829-834). There were also reports suggesting that lipocalin-2 is an early marker of acute kidney damage (Mishra, J., et al. Lancet 365:1231-1238 (2005)). It has been discovered that elevated circulating levels of lipocalin-2 plays a causative role in the pathogenesis of obesity and/or obesity-induced metabolic disorders. Although many tissues have previously been shown to express lipocalin-2, it has been discovered that adipose tissue and liver are probably the two principal sources that contribute to the elevated circulating levels of this protein in obesity states.

In db/db obese mice, increased serum levels of lipocalin-2 are associated with the selective elevation of its mRNA expression in adipose tissue and liver (FIG. 1). In human subjects, lipocalin-2 levels are positively correlated with several parameters of adiposity, including BMI, waist circumference and fat percentage (Table 2), suggesting that the increased fat mass might also account for the elevated circulating concentrations of this protein in obese individuals. In line with the results, several previous in vitro studies have demonstrated the abundant expression of lipocalin-2 in adipocytes (Kratchmarova, I. K, et al. Mol Cell Proteomics, 1:213-222 2002)) and macrophages (Meheus, L. A., et al., J

*Immunol.* 151:1535-1547 (1993)). Furthermore, its expression is sharply induced following conversion of preadipocytes to mature adipocytes, or stimulation with inflammatory factors (Baudry, A., Yang, Z. Z., and Hemmings, B. A. *J Cell Sci.* 119:889-897 (2006); Jessen, B. A., and Stevens, G. J., *Gene,* 299:95-100 (2002).

The data show that long-term treatment with recombinant lipocalin-2 induces glucose intolerance and insulin resistance in C57 mice (FIGS. 3A-3B). These adverse effects might be attributable to the ability of lipocalin-2 to induce triglyceride accumulation in skeletal muscle and liver tissue. Excessive lipid accumulation in skeletal muscle and liver are critical early steps in the development of insulin resistance (Marchesini, G., et al. *Curr Opin Lipidol.* 16:421-427 (2005); Perseghin, G., *Curr Opin Lipidol.* 16:416-420 (2005)). The metabolically active long-chain fatty acyl CoAs, ceramides and diacylglycerols have been shown to impair insulin signaling either directly or via chronic translocation/activation of mediators such as a protein kinase C$\theta$ and $\phi$ (Hulver, M. W., and Dohm, G. L., *Proc Nutr Soc,* 63:375-380 (2004); Hegarty, B. D., et al. *Acta Physiol Scand* 178:373-383 (2003)). The results from the animal study have shown that lipocalin-2 can induce expression of FATP1 and 4, the two fatty acid transport proteins that have recently been shown to play an important role in obesity-induced intramuscular lipid accumulation and insulin resistance (Fisher, R. M., and Gertow, K., *Curr Opin Lipidol,* 16:173-178 (2005)). In addition, it decreases the abundance of acyl-CoA oxidase and UCP2, two genes involved in fatty acid oxidation in skeletal muscle (Lowell, B. B., and Spiegelman, B. M., *Nature,* 404:652-660 (2000); Kersten, S., et al., *J Clin Invest.* 103:1489-1498 (1999)). This in vivo data is further supported by our findings that chronic treatment with lipocalin-2 causes enhanced fatty acid uptake and decreased fatty acid oxidation in L6 myotube, which lead to intramuscular lipid accumulation. These changes are associated with a significant reduction in glucose uptake. Although it is not statistically significant, a modest decrease in insulin-stimulated glucose uptake at 48 and 72 h after lipocalin-2 treatments was also observed. One explanation for this finding is that lipocalin-2-induced insulin resistance might be secondary to elevated intra-muscular lipid accumulation, and thus needs longer treatment period to observe its obvious effect. Unfortunately, L6 myotubes is unable to survive for more than 72 h in the serum-free condition. This technical bottleneck makes it difficult to test the hypothesis in this in vitro system.

Unlike its actions in skeletal muscle, lipocalin-2 has no obvious effect on expression of those key genes involved in fatty acid metabolism in liver. The mild increase in hepatic lipid is probably secondary to the changes in systemic lipid metabolism, or via a mechanism distinct from those observed in skeletal muscle. Lipocalin-2 increases hepatic expression of PEPCK and G6P, the two key genes involved in gluconeogenesis. This effect might also contribute to lipocalin-2-induced hyperglycemia and insulin resistance in mice. In addition to its direct actions on muscle and liver, lipocalin-2 might also indirectly exert its adverse metabolic effect by decreasing serum levels of the anti-diabetic hormone adiponectin (Table 4). In contrast to lipocalin-2, adiponectin enhances fatty acid oxidation and energy dissipation, decreases lipid accumulation in both liver and skeletal muscle, and increase insulin sensitivity in these two tissues (Tomas, E., et al., *Proc Natl Acad Sci USA* 99:16309-16313); Yamauchi, T., et al., *Nat Med,* 7:941-946 (2001)). In addition, adiponectin has been shown to inhibit hepatic glucose production by suppressing PEPCK and G6P mRNA expression, an effect opposite to that of lipocalin-2 observed in this study.

In agreement with the animal data, clinical data has also shown a marked elevation of circulating lipocalin-2 in human obese subjects, a finding reminiscent of many insulin resistance-inducing adipokines and cytokines (Berg, A. H., and Scherer, P. E., *Circ Res,* 96:939-949 (2005); Wellen, K. E., and Hotamisligil, G. S., *J Clin Invest,* 115:1111-1119 (2005)). Furthermore, a close positive association between lipocalin-2 levels and several parameters for obesity-related metabolic disorders, including adverse lipid profiles (elevated serum triglyceride and decreased HDL-cholesterol), hyperinsulinemia, fasting glucose levels and HOMA-IR were observed. The correlation of lipocalin-2 with fasting glucose and HOMA-IR remains significant even after adjusting for BMI, suggesting that this protein might be an independent risk factor for hyperglycemia and insulin resistance in humans.

In summary, the data provided herein has provided the first evidence supporting the role of lipocalin-2 as a circulating mediator of obesity-induced insulin resistance, possibly by increasing ectopic lipid accumulation in skeletal muscle and liver. The insulin-sensitizing effects of the PPAR$\gamma$ agonists might be partly mediated by the suppression of lipocalin-2 production. Furthermore, the clinical data demonstrates that lipocalin-2 is a useful serum biomarker for adiposity and insulin resistance in human subjects. These results collectively demonstrate that lipocalin-2 represents a therapeutic target for the treatment of obesity-induced insulin resistance and other metabolic abnormalities.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for diagnosing that a subject is at risk of developing an obesity-induced metabolic disorder comprising:

obtaining a sample from a subject to be diagnosed;

determining the lipocalin-2 level contained in the sample;

comparing the lipocalin-2 level to a positive reference level obtained from adults confirmed to have an obesity-induced metabolic disorder; and diagnosing that the subject is at risk of developing an obesity-induced metabolic disorder based on a lipocalin-2 level contained in the sample that is greater than or within a range of plus or minus 10% of the positive lipocalin-2 reference level obtained from adults confirmed to have an obesity-induced metabolic disorder.

2. The method of claim 1, wherein the obesity-induced metabolic disorder is selected from the group consisting of hyperinsulinemia, atherosclerosis, insulin resistance, and Type 2 diabetes.

3. The method of claim 1, wherein the lipocalin-2 level in the sample is determined by an immunoassay.

4. The method of claim 1 wherein the sample is selected from the group consisting of blood, urine, saliva, cerebrospinal fluid and tissue.

5. The method of claim 1 wherein the obesity induced metabolic disorder is diabetes.

* * * * *